United States Patent [19]

Lee

[11] Patent Number: 5,821,056
[45] Date of Patent: Oct. 13, 1998

[54] GROWTH DIFFERENTIATION FACTOR-9

[75] Inventor: Se-Jin Lee, Baltimore, Md.

[73] Assignee: The Johns Hopkins University School of Medicine, Baltimore, Md.

[21] Appl. No.: 491,835

[22] PCT Filed: Jan. 12, 1994

[86] PCT No.: PCT/US94/00685

§ 371 Date: Oct. 23, 1995

§ 102(e) Date: Oct. 23, 1995

[87] PCT Pub. No.: WO94/15966

PCT Pub. Date: Jul. 21, 1994

Related U.S. Application Data

[63] Continuation-in-part of Ser. No. 3,303, Jan. 12, 1993, abandoned.

[51] Int. Cl.[6] .......................... C07K 14/475; C12N 1/21; C12N 5/10; C12N 15/12

[52] U.S. Cl. .............................. 435/6; 530/350; 530/397; 530/399; 536/23.51; 536/23.5; 536/24.31; 435/252.3; 435/325; 435/320.1; 435/7.1

[58] Field of Search ..................................... 530/350, 397, 530/399; 435/69.4, 69.1, 172.3, 240.1, 252.3, 320.1, 325, 6, 7.1; 534/23.51, 23.5, 23.1, 24.31; 514/2, 8, 12

[56] References Cited

PUBLICATIONS

Bowie et al. Science 247:1307–1310, 1990.
Rudinger. Peptide Hormones, Parsons, ed., University Park Press, Baltimore, pp. 1–7, 1976.
Wells. Biochemistry 29:85–7–17., 1990.
Ngo et al. The Protein Folding and Tertiary Structure Prediction. Merz et al., eds., Birkhauser, Boston, pp. 491–495, 1994.
Massague. Cell 49:437–8, 1987.
Callard et al. The Cytokine FactsBook, Academic Press, London, pp. 31–32, 1994.

*Primary Examiner*—Elizabeth C. Kemmerer
*Attorney, Agent, or Firm*—Fish & Richardson, P.C.

[57] ABSTRACT

Growth differentiation factor-9 (GDF-9) is disclosed along with its polynucleotide sequence and amino acid sequence. Also disclosed are diagnostic and therapeutic methods of using the GDF-9 polypeptide and polynucleotide sequences.

14 Claims, 15 Drawing Sheets

```
  1  ATGGGTTCCTTCTTAGTTCTTCCAAGTCATGGCACTTCCTGTTGGGGT    60
        M  A  L  P  S  N  F  L  L  G  V
 61  TTGCTGCTTTGCCTGTGTTTCTTAGTAGCCTTCAGGTTCTACTGAAGA   120
      C  C  F  A  W  L  C  F  L  S  S  Q  A  S  T  E  E
121  ATCCCAGAGTGGAGCCAGTGAAAATGGAGTCGAGGCAGACCCCTGGTCCTGCT   180
      S  Q  S  G  A  S  E  N  V  E  S  E  A  D  P  W  S  L  L  L
181  GCCTGTAGATGGGACTGACAGGTCTGGCCCCTTGCCCCCCTCTTTAAGGTTCTATCTGA   240
      P  V  D  G  T  D  R  S  G  L  P  P  L  F  K  V  L  S  D
241  TAGGCGAGGTGAGACCCCTAAGCTGCAGCTGCAGCCCTGACTCTACTACATGAAAAA   300
      R  R  G  E  T  P  K  L  Q  P  D  S  R  A  L  Y  Y  M  K  K
301  GCTCTATAAGACGTATGCTACCAAAGAGGGGTTCCAAACCCAGCAGGAAGTCACCTCTA   360
      L  Y  K  T  Y  A  T  K  E  G  V  P  K  P  S  R  S  H  L  Y
361  CAATACCGTCCGGCTCTTCAGTCCCTGTGCCCAGCAGCAGCAGGAACCAGGT   420
      N  T  V  R  L  F  S  P  C  A  Q  Q  E  Q  A  P  S  N  Q  V
421  GACAGGACCGCTGCCGATGGTGGACCTGCTGTTTAACCTGGACTGCCATGGA   480
      T  G  P  L  P  M  V  D  L  L  F  N  L  D  R  V  T  A  M  E
481  ACACTTGCTGAAATCGGTCTCTGCTATACACTCTGAACACTGGCCTCTTCCTCCTCCAC   540
      H  L  L  K  S  V  L  L  Y  T  L  N  N  S  A  S  S  S  S  T
541  TGTGACCTGTATGTGACCTGTGGTAAAGGAGGCCATGTCTTCTGCAGGCCACCCCCC   600
      V  T  C  M  C  D  L  V  V  K  E  A  M  S  S  G  R  A  P  P
```

FIG. 2A

```
601   AAGAGCACCGTACTCATTCACCCTGAAGAAACACAGATGGATTGAGATTGACGTC   660
      R   A   P   Y   S   F   T   L   K   K   H   R   W   I   E   I   D   V   T   S
661   CCTCCTTCAGCCCCCTAGTGACCTCCAGCGAGGAGCATTCACCTGTCTGTCAATTTTAC   720
      L   L   Q   P   L   V   T   S   S   E   R   S   I   H   L   S   V  [N   F   T]
721   ATGCACAAAAGACCAGGTGCCAGAGACGGAGTGTTTAGCATGCCTCTCAGTGCCTCC   780
      C   T   K   D   Q   V   P   E   D   G   V   F   S   M   P   L   S   V   P   P
781   TTCCCTCATCTTGTATCTCAACGACACAGCCTTTACAGCCCTTTACAGGCCATCATCCCGGCCTTGGCAGTCTCT   840
      S   L   I   L   Y   L  [N   D   T]  S   T   Q   A   Y   H   S   W   Q   S   L
841   TCAGTCCACCTGGAGGCCTTTACAGCATCCCGGCCAGCCCGTGTGCCCGTCCCGT   900
      Q   S   T   W   R   P   L   Q   H   P   G   Q   A   G   V   A   A   R   P   V
901   GAAAGAGGAAGCTACTGAGGTGGAAGATCTCCCGGCCGAGGGCCAGAAAGCCAT   960
      K   E   E   A   T   E   V   E   R   S   P  [R   R   R]  G   Q   K   A   I
961   CCGCTCCGAAGCCGAAGGGGCCACTTCTTACAGCATCCTTACAGCTTCAGCGAATACTTCAA   1020
      R   S   E   A   K   G   P   L   L   T   A   S  [F   N   L   S]  E   Y   F   K
1021  ACAGTTTCTTTCCCCAAAACGAGTGTGAACTCCATGACTTCAGACTTCAGAGTTTTAGTCA   1080
      Q   F   L   F   P   Q   N   E   C   E   L   H   D   F   R   L   S   F   S   Q
1081  GCTCAAATGGGACAACTGGATCGTGGCCCCACAGTACAACCCTAGGTACTGTAAAGG   1140
      L   K   W   D   N   W   I   V   A   P   H   R   Y   N   P   R   Y   C   K   G
```

FIG. 2B

```
1141  GGACTGTCCTAGGGCCGGTCAGGCATCGGTATGGCTCTCCTGTGCACACCATGTCCAGAA  1200
       D  C  P  R  A  V  R  H  R  Y  G  S  P  V  H  T  M  V  Q  N
1201  TATAATCTATGAGAAGCTGGACCCCTTCAGTGCCCTTCGTGTGCCGGGCAAGTA        1260
       I  I  Y  E  K  L  D  P  S  V  P  R  P  S  C  V  P  G  K  Y
1261  CAGCCCCCCTGAGTGTGTGACCATTGAACCCGACGGCTCCATCGCTTACAAAGAGTACGA  1320
       S  P  L  S  V  L  T  I  E  P  D  G  S  I  A  Y  K  E  Y  E
1321  AGACATGATAGCTACGAGTGCACCTGTCGTTAGCATGGGGCCACTTCAACAAGCCTGC    1380
       D  M  I  A  T  R  C  T  C  R  *
1381  CTGGCAGAGCAATGCTGTGGGCCTTAGAGTGCCTGGCCAGAGAGCTTCCTGTGACCAGTC  1440
1441  TCTCCGTGCTGCTCAGTGCCACACACTGTGTGTGTGGATGAGCA                  1500
1501  CATCGAGTGCAGTGTCCGTAGGTGTAAAGGGCACACTCACTGGTTCGTTGCCATAAACCAA 1560
1561  GTGAAATGTAACTCATTTGGAGAGCTCTTTCTCCCACGAGTGTAGTTTTCAGTGGACAG   1620
1621  ATTTGTTAGCATAAGTCTCGAGTAGAATGTAGCTGTGAACATGTCAGAGTGCTGTGTTT   1680
1681  TATGTGACGGAAGAATAAACTGTTGATGGCAT  1712
```

FIG. 2C

```
GDF-3       KRRAAISVPKGFC--RNFHRHQLFINF-QDLGWHKWVIAPKGFMANYCHGECPFSMTTYLNS----
GDF-9       FNLSEYFKQFLFP--QNECELHDFRLSF-SQLKWDNWIVAPHRYNPRYCKGDCPRAVRHRYGS----

GDF-1       PRRDAEPVLGGGP--GGACRARRLYVSF-REVGWHRWVIAPRGFLANYCQGQCALPVALSGSGP
Vg-1        RRKRSYSKLPFTA--SNICKKRHLYVEF-KDVGWQNWVIAPQGYMANYCYGECPYPLTEILNG---
Vgr-1       RVSSASDYNSSEL--KTACRKHELYVSF-QDLGWQDWIIAPKGYAANYCDGECSFPLNAHMNA---
OP-1        RMANVAENSSSDQ--RQACKKHELYVSF-RDLGWQDWIIAPEGYAAYYCEGECAFPLNSYMNA---
BMP-5       RMSSVGDYNTSEQ--KQACKKHELYVSF-RDLGWQDWIIAPEGYAAFYCDGECSFPLNAHMNA---
60A         SPNNVPLLEPMES--TRSCQMQTLYIDF-KDLGWHDWIIAPEGYGAFYCSGECNFPLNAHMNA---
BMP-2       EKRQAKHKQRKRL--KSSCKRHPLYVDF-SDVGWNDWIVAPPGYHAFYCHGECPFPLADHLNS---
BMP-4       RSPKHHSQRARKK--NKNCRRHSLYVDF-SDVGWNDWIVAPPGYQAFYCHGDCPFPLADHLNS---
DPP         KRHARRPTRRKNH--DDTCRRHSLYVDF-SDVGWDDWIVAPLGYDAYYCHGKCPFPLADHFNS---
BMP-3       QTLKKARRKQWIE--PRNCARRYLKVDF-ADIGWSEWIISPKSFDAYYCSGACQFPMPKSLKP---
MIS         PGRAQRSAGATAA--DGPCALRELSVDL----RAERSVLIPETYQANNCQGVCGWPQSDRNPRY-
Inhibin α    LRLLQRPPEEPAA--HANCHRVALNISF-QELGWERWIVYPPSFIFHYCHGGCGLHIPPNLSLPV
Inhibin βA   RRRRRGLECDGKV--NICCKKQFFVSF-KDIGWNDWIIAPSGYHANYCEGECPSHIAGTSGSSL
Inhibin βB   RIRKRGLECDGRT--NLCCRQQFFIDF-RLIGWNDWIIAPTGYYGNYCEGSCPAYLAGVPGSAS
TGF-β1      RRALDTNYCFSST--EKNCCVRQLYIDFRKDLGWK-WIHEPKGYHANFCLGPCPYIWSLD-----
TGF-β2      KRALDAAYCFRNV--QDNCCLRPLYIDFRKDLGWK-WIHEPKGYNANFCAGACPYLWSSD-----
TGF-β3      KRALDTNYCFRNL--EENCCVRPLYIDFRKDLGWK-WVHEPKGYYANFCSGPCPYLRSAD-----
TGF-β4      RRDLDTDYCFGPGTDEKNCCVRPLYIDFRQDLGWK-WIHEPKGYMANFCMGPCPYIWSAD-----
TGF-β5      KRGVGQEYCFGNN--GPNCCVKPLYINFRKDLGWK-WIHEPKGYEANYCLGNCPYIWSMD-----
```

FIG. 3A

```
GDF-3     --SNYAFMQALMHM---ADPKVPKAVGV--PTKLSPISMLYQ-DSDKNVILRHYEDMVVDE C G
GDF-9     --PVHTMVQNIIYE---KLDPSVPRPSCV--PGKYSPLSVLTI-EPDGSIAYKEYEDMIATR C R

GDF-1     PALNHAVLRALMHA---AAPGAADLPCCV--PARLSPISVLFF-DNSDNVVLRQYEDMVVDE C R
Vg-1      --SNHAILQTLVHS---IEPEDIPLPCCV--PTKMSPISMLFY-DNNDNVVLRHYENMAVDE C H
Vgr-1     --TNHAIVQTLVHL---MNPEYVPKPCCA--PTKLNAISVLYF-DDNSNVILKKYRNMVVRA C H
OP-1      --TNHAIVQTLVHF---INPETVPKPCCA--PTQLNAISVLYF-DDSSNVILKKYRNMVVRA C H
BMP-5     --TNHAIVQTLVHL---MFPDHVPKPCCA--PTKLNAISVLYF-DDSSNVILKKYRNMVVRS C H
60A       --TNHAIVQTLVHL---LEPKKVPKPCCA--PTRLGALPVLYH-LNDENVNLKKYRNMIVKS C H
BMP-2     --TNHAIVQTLVNS---VNSKIPKACCV--PTELSAISMLYL-DENEKVVLKNYQDMVVEG C R
BMP-4     --TNHAIVQTLVNS---VNSSIPKACCV--PTELSAISMLYL-DEYDKVVLKNYQEMVVEG C R
DPP       --TNHAVVQTLVNN---MNPGKVPKACCV--PTQLDSVAMLYL-NDQSTVVLKNYQEMTVVG C R
BMP-3     --SNHATIQSIVRA-VGVVPGIPEPCCV--PEKMSSLSILFF-DENKNVVLKVYPNMTVES C R
MIS       --GNHVLLLKMQA---RGAALARPPCCV--PTAYAGKLLISLSEER--ISAHHVPNMVATE C R
Inhibin α --PGAPPTPAQPYS---LLPGAQPCCAALPGTMRPLHVRTTSDGGYSFKYETVPNLLTQH C I
Inhibin βA--SFHSTVINHYRMRGHSPFANLKSCCV--PTKLRPMSMLYY-DDGQNIIKKDIQNMIVEE C G
Inhibin βB--SFHTAVVNQYRMRGLNPGT-VNSCCI--PTKLSTMSMLYF-DDEYNIVKRDVPNMIVEE C G
TGF-β1    --TQYSKVLALYNQ---HNPGASAAPCCV--PQALEPLPIVYY-VGRKPKV-EQLSNMIVRS C K
TGF-β2    --TQHSRVLSLYNT---INPEASASFCCV--SQDLEPLTILYY-IGKTPKI-EQLSNMIVKS C K
TGF-β3    --TTHSTVLGLYNT---LNPEASASPCCV--PQDLEPLTILYY-VGRTPKV-EQLSNMVVKS C S
TGF-β4    --TQYTKVLALYNQ---HNPGASAAPCCV--PQTLDPLPIIYY-VGRNVRV-EQLSNMVVRA C K
TGF-β5    --TQYSKVLSLYNQ---NNPGASISPCCV--PDVLEPLPIIYY-VGRTAKV-EQLSNMVVRS C S
```

FIG. 3B

|  | GDF-3 | GDF-9 | GDF-1 | Vg-1 | Vgr-1 | OP-1 | BMP-5 | 60A | BMP-2 | BMP-4 | DPP |
|---|---|---|---|---|---|---|---|---|---|---|---|
| TGF-β5 | 36 | 25 | 32 | 34 | 37 | 36 | 36 | 36 | 35 | 33 | 35 |
| TGF-β4 | 33 | 22 | 34 | 32 | 39 | 37 | 36 | 38 | 33 | 32 | 33 |
| TGF-β3 | 32 | 25 | 33 | 37 | 39 | 38 | 36 | 40 | 36 | 35 | 35 |
| TGF-β2 | 31 | 25 | 32 | 36 | 37 | 38 | 35 | 39 | 34 | 33 | 35 |
| TGF-β1 | 36 | 23 | 33 | 34 | 35 | 34 | 34 | 38 | 35 | 34 | 35 |
| INHIBIN βB | 41 | 31 | 35 | 37 | 41 | 42 | 37 | 39 | 42 | 42 | 42 |
| INHIBIN βA | 42 | 30 | 37 | 44 | 44 | 43 | 43 | 36 | 42 | 41 | 39 |
| INHIBIN α | 25 | 27 | 23 | 22 | 25 | 24 | 24 | 24 | 22 | 22 | 19 |
| MIS | 22 | 21 | 34 | 30 | 24 | 27 | 24 | 25 | 27 | 27 | 25 |
| BMP-3 | 42 | 29 | 42 | 49 | 44 | 42 | 43 | 41 | 48 | 47 | 43 |
| DPP | 47 | 32 | 41 | 48 | 59 | 58 | 57 | 54 | 74 | 75 | 100 |
| BMP-4 | 50 | 34 | 43 | 56 | 60 | 58 | 59 | 54 | 92 | 100 | - |
| BMP-2 | 53 | 33 | 42 | 58 | 61 | 60 | 61 | 57 | 100 | - | - |
| 60A | 47 | 30 | 41 | 51 | 71 | 69 | 74 | 100 | - | - | - |
| BMP-5 | 50 | 31 | 46 | 56 | 91 | 88 | 100 | - | - | - | - |
| OP-1 | 50 | 30 | 47 | 57 | 87 | 100 | - | - | - | - | - |
| Vgr-1 | 53 | 31 | 46 | 58 | 100 | - | - | - | - | - | - |
| Vg-1 | 57 | 30 | 57 | 100 | - | - | - | - | - | - | - |
| GDF-1 | 50 | 27 | 100 | - | - | - | - | - | - | - | - |
| GDF-9 | 33 | 100 | - | - | - | - | - | - | - | - | - |
| GDF-3 | 100 | - | - | - | - | - | - | - | - | - | - |

FIG. 4A

| | BMP-3 | MIS | INHIBIN α | INHIBIN βA | INHIBIN βB | TGF-β1 | TGF-β2 | TGF-β3 | TGF-β4 | TGF-β5 |
|---|---|---|---|---|---|---|---|---|---|---|
| TGF-β5 | 30 | 26 | 24 | 36 | 28 | 82 | 70 | 73 | 79 | 100 |
| TGF-β4 | 27 | 29 | 24 | 33 | 30 | 86 | 68 | 74 | 100 | - |
| TGF-β3 | 32 | 25 | 24 | 36 | 37 | 78 | 82 | 100 | - | - |
| TGF-β2 | 32 | 23 | 22 | 37 | 34 | 74 | 100 | - | - | - |
| TGF-β1 | 32 | 28 | 23 | 41 | 35 | 100 | - | - | - | - |
| INHIBIN βB | 37 | 25 | 25 | 63 | 100 | - | - | - | - | - |
| INHIBIN βA | 36 | 24 | 26 | 100 | - | - | - | - | - | - |
| INHIBIN α | 29 | 18 | 100 | - | - | - | - | - | - | - |
| MIS | 30 | 100 | - | - | - | - | - | - | - | - |
| BMP-3 | 100 | - | - | - | - | - | - | - | - | - |
| DPP | - | - | - | - | - | - | - | - | - | - |
| BMP-4 | - | - | - | - | - | - | - | - | - | - |
| BMP-2 | - | - | - | - | - | - | - | - | - | - |
| 60A | - | - | - | - | - | - | - | - | - | - |
| BMP-5 | - | - | - | - | - | - | - | - | - | - |
| OP-1 | - | - | - | - | - | - | - | - | - | - |
| Vgr-1 | - | - | - | - | - | - | - | - | - | - |
| Vg-1 | - | - | - | - | - | - | - | - | - | - |
| GDF-1 | - | - | - | - | - | - | - | - | - | - |
| GDF-9 | - | - | - | - | - | - | - | - | - | - |
| GDF-3 | - | - | - | - | - | - | - | - | - | - |

FIG. 4B

```
  1 MAL?SNFLLGVCCFAWLCFLSSLSSQASTEESQSGASENVESEADPWSLL  50
    || |   |||  |||||||  ||  ||||   ||   ||   || | |||||
  1 MAR?NKFLLWFCCFAWLCFPISLGSQASGGEAQIAASAELESGAMPWSLL  50

51 LPVDGTDRSGLLPPLFKVLSDRRGETPKLQPDSRALYYMKKLYKTYATKE 100
    |   ||  ||||  |||||| ||    ||  | ||||||| |||||||||||||
 51 QHIDERDRAGLLPALFKVLSVGRGGSPRLQPDSRALHYMKKLYKTYATKE 100

101 GVPKPSRSHLYNTVRLFSPCAQQEQAPSNQVTGPLPMVDLLFNLDRVTAM 150
    | ||  ||||||||||| ||   |||   |||| || | |||||||| |
101 GIPKSNRSHLYNTVRLFTPCTRHKQAPGDQVTGILPSVELLFNLDRITTV 150

151 EHLLKSVLLYTLNNSASSSSTVTCMCDLVVKEAMSSGRAPPRAPYSFTL. 199
    ||||||||||  |||  | ||  |  |  ||   ||  ||   |||||||
151 EHLLKSVLLYNINNSVSFSSAVKCVCNLMIKEPKSSSRTLGRAPYSFTFN 200

200 ......KKHRWIEIDVTSLLQPLVTSSERSIHLSVNFTCTKDQV....PE 239
          ||| || |||||||||||| |    ||||  | ||||  |||
201 SQFEFGKKHKWIQIDVTSLLQPLVASNKRSIHMSINFTCMKDQLEHPSAQ 250

240 DGVFSMPLSVPPSLILYLNDTSTQAYHSWQSLQSTWRPLQHPGQA.GVAA 288
    |  |  |  ||||||||||||| ||||| ||  ||   ||  |    |
251 NGLFNMTL.VSPSLILYLNDTSAQAYHSWYSLHYKRRPSQGPDQERSLSA 299

289 RPVKEEATEVERSP..RRRRGQKAIRSEAKGPLLTASFNLSEYFKQFLFP 336
    || ||| |  ||   | ||||  | | ||  ||||||||||| ||| |
300 YPVGEEAAEDGRSSHHRHRRGQETVSSELKKPLGPASFNLSEYFRQFLLP 349

337 QNEEELHDFRLSFSQLKWDNWIVAPHRYNPRYCKGDCPRAVRHRYGSPVH 386
    ||||||||||||||||||||||||||||||||||||||||| ||||||||
350 QNEEELHDFRLSFSQLKWDNWIVAPHRYNPRYCKGDCPRAVGHRYGSPVH 399

387 TMVQNIIYEKLDPSVPRPSCVPGKYSPLSVLTIEPDGSIAYKEYEDMIAT 436
    |||||||||||| ||||||||| |||||||||||||||||||||||||||
400 TMVQNIIYEKLDSSVPRPSCVPAKYSPLSVLTIEPDGSIAYKEYEDMIAT 449

437 RCTCR 441
    | | |
450 KCTCR 454
```

FIG. 6

FIG. 7A
FIG. 7B
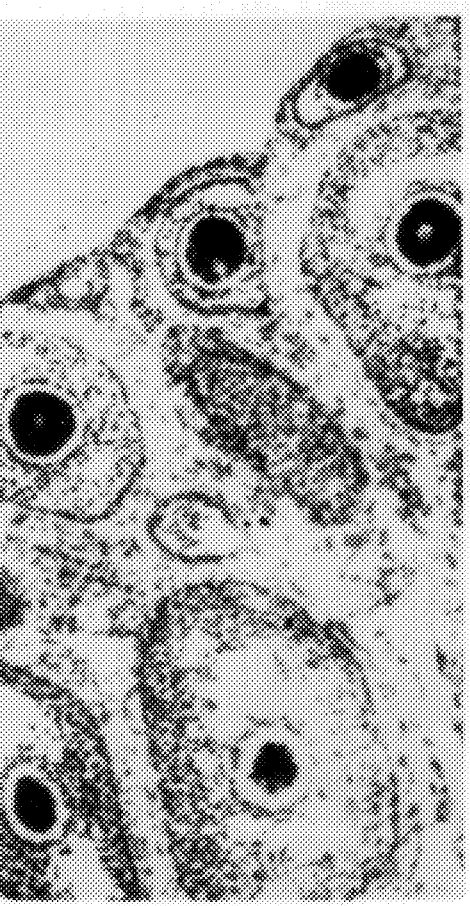
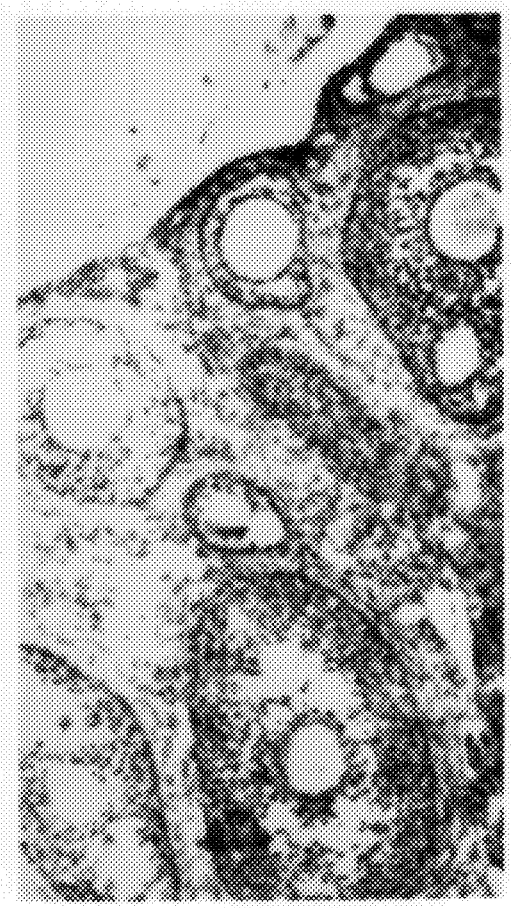
FIG. 7C
FIG. 7D

GROWTH DIFFERENTIATION FACTOR-9

This application is a 371 application of PCT US94/00685, filed Jan. 12, 1994, which is a continuation-in-part of U.S. Ser. No. 08/003,303, filed Jan. 12, 1993, now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-9 (GDF-9).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature*, 345:167, 1990), *Drosophila* decapentaplegic (DPP) gene product, which is required for dorsal-ventral axis formation and morphogenesis of the imaginal disks (Padgett, et al., *Nature*, 325:81–84, 1987), the Xenopus Vg-1 gene product, which localizes to the vegetal pole of eggs ((Weeks, et al., *Cell*, 51:861–867, 1987), the activins (Mason, et al., *Biochem, Biophys. Res. Commun.*, 135:957–964, 1986), which can induce the formation of mesoderm and anterior structures in Xenopus embryos (Thomsen, et al., *Cell*, 63:485, 1990), and the bone morphogenetic proteins (BMPs, osteogenin, OP-1) which can induce de novo cartilage and bone formation (Sampath, et al., *J. Biol. Chem.*, 265:13198, 1990). The TGF-βs can influence a variety of differentiation processes, including adipogenesis, myogenesis, chondrogenesis. hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., *Nature*, 321:779, 1986) and the TGF-, βs (Cheifetz, et al., *Cell*, 48:409, 1987), heterodimers have also been detected, and these appear to have different biological properties than the respective homodimers.

The inhibins and activins were originally purified from follicular fluid and shown to have counteracting effects on the release of follicle-stimulating hormone by the pituitary gland. Although the mRNAs for all three inhibin/activin subunits (αa, βA and βB) have been detected in the ovary, none of these appear to be ovary-specific (Meunier, et al., *Proc.Natl.Acad.Sci. USA*, 85:247,1988). MIS has also been shown to be expressed by granulosa cells and the effects of MIS on ovarian development have been documented both in vivo in transgenic mice expressing MIS ectopically (Behringer, supra) and in vitro in organ culture (Vigier, et al., *Development*, 100:43, 1987).

Identification of new factors that are tissue-specific in their expression pattern will provide a greater understanding of that tissue's development and function.

SUMMARY OF THE INVENTION

The present invention provides a cell growth and differentiation factor, GDF-9, a polynucleotide sequence which encodes the factor and antibodies which are immunoreactive with the factor. This factor appears to relate to various cell proliferative disorders, especially those involving ovarian tumors, such as granulosa cell tumors.

Thus, in one embodiment, the invention provides a method for detecting a cell proliferative disorder of ovarian origin and which is associated with GDF-9. In another embodiment, the invention provides a method of treating a cell proliferative disorder associated with abnormal levels of expression of GDF-9, by suppressing or enhancing GDF-9 activity.

BRIEF DESCRIPTION OF THE DRAWINGS

FIG. 2a–c shows nucleotide and predicted amino acid sequence of murine GDF-9 (SEQ ID NO:3 and SEQ ID No:4, respectively). Consensus N-glycosylation signals are denoted by plain boxes. The putative tetrabasic processing sites are denoted by stippled boxes. The in-frame termination codons upstream of the putative initiating ATG and the consensus polyadenylation signals are underlined. The poly A tails are not shown. Numbers indicate nucleotide position relative to the 5' end.

FIG. 3a and FIG. 3b shows the alignment of the C-terminal sequences of GDF-9 with other members of the TGF-β family (SEQ ID NO:5-25). The conserved cysteine residues are shaded. Dashes denote gaps introduced in order to maximize alignment.

FIG. 4a and FIG. 4b shows amino acid homologies among the different members of the TGF-β superfamily. Numbers represent percent amino acid identities between each pair calculated from the first conserved cysteine to the C-terminus. Boxes represent homologies among highly-related members within particular subgroups.

FIG. 6 shows a comparison of the predicted amino acid sequences of murine (top lines) and human (bottom lines) GDF-9 (SEQ ID NO:4 and SEQ ID NO:26, respectively). Numbers represent amino acid positions relative to the N-termini. Vertical lines represent sequence identities. Dots represent gaps introduced in order to maximize the alignment. The clear box shows the predicted proteolytic processing sites. The shaded boxes show the cysteine residues in the mature region of the proteins. The bars at the bottom show a schematic of the pre-(clear) and mature (shaded) regions of GDF-9 with the percent sequence identities between the murine and human sequences shown below.

FIG. 7 shows in situ hybridization to adult ovary sections using a GOF-9 RNA probe. [$^{35}$S]-labeled anti-sense (FIGS.

7a and 7c) or sense (FIGS. 7b and 7d) GDF-9 RNA probes were hybridized to adjacent paraffin-embedded sections of ovaries fixed in 4% paraformaldehyde. Sections were dipped in photographic emulsion, exposed, developed, and then stained with hematoxylin and eosin. Two representative fields are shown.

Figure 8A:
Figure 8B:
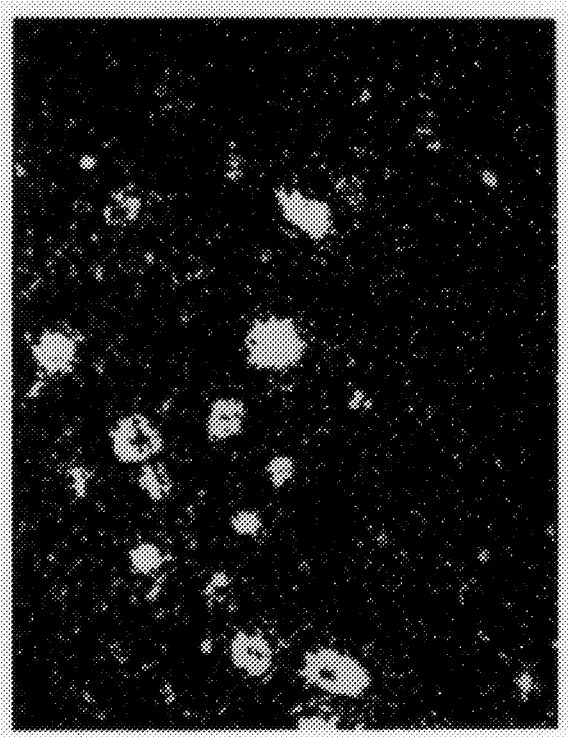

FIG. 8 shows in situ hybridization to a postnatal day 4 ovary section using an antisense GDF-9 RNA probe. Sections were prepared as described for FIG. 7. Following autoradiography and staining, the section was photographed under bright-field (FIG. 8a) or dark-field (FIG. 8b) illumination.

Figure 9A:
Figure 9B:

FIG. 9 shows in situ hybridization to postnatal day 8 ovary sections using an antisense (FIG. 9a) or sense (FIG. 9b) GDF-9 RNA probe. Sections were prepared as described for FIG. 7.

Figure 10A:
Figure 10B:
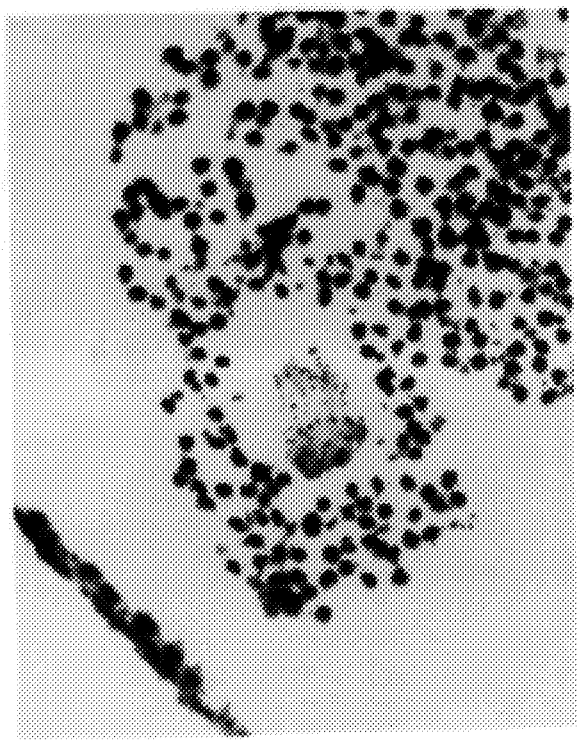

FIG. 10 shows in situ hybridization to adult oviduct sections using an antisense (FIG. 10a) or sense (FIG. 10b) GDF-9 RNA probe. Sections were prepared as described for FIG. 7.

Figure 11A:
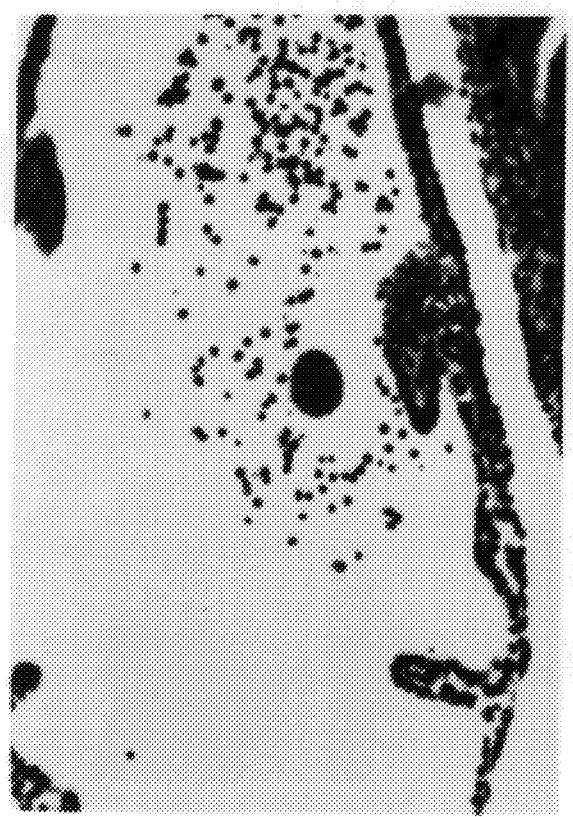
Figure 11B:
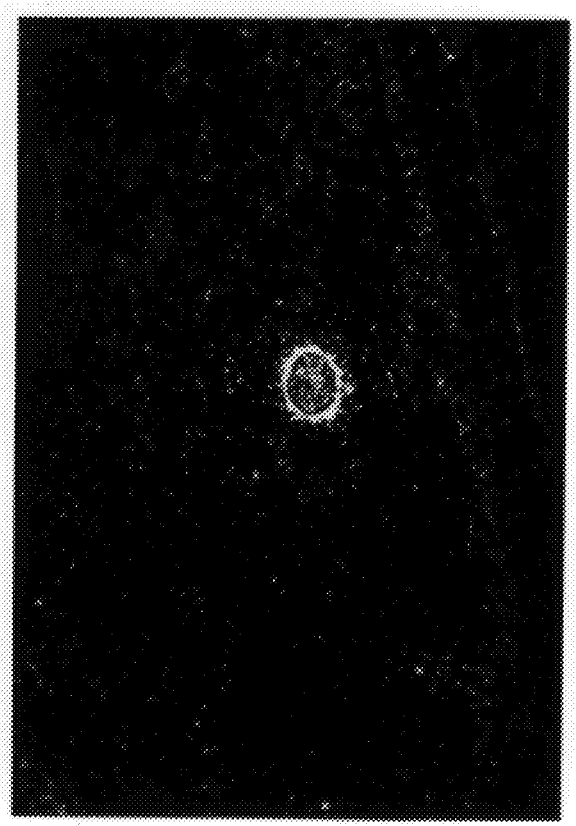

FIG. 11 shows in situ hybridization to an adult oviduct (0.5 days following fertilization) section using an antisense GDF-9 RNA probe. Sections were prepared as described for FIG. 7. Following autoradiography and staining, the section was photographed under bright-field (FIG. 11a) or dark-field (FIG. 11b) illumination.

DETAILED DESCRIPTION OF THE INVENTION

The present invention provides a growth and differentiation factor, GDF-9 and a polynucleotide sequence encoding GDF-9. Unlike other members of the TGF-β superfamily, GDF-9 expression is highly tissue specific, being expressed in cells primarily in ovarian tissue. In one embodiment, the invention provides a method for detection of a cell proliferative disorder of the ovary, which is associated with GDF-9 expression. In another embodiment, the invention provides a method for treating a cell proliferative disorder associated with abnormal expression of GDF-9 by using an agent which suppresses or enhances GDF-9 activity.

The TGF-β superfamily consists of multifunctionaly polypeptides that control proliferation, differentiation, and other functions in many cell types. Many of the peptides have regulatory, both positive and negative, effects on other peptide growth factors. The structural homology between the GDF-9 protein of this invention and the members of the TGF-β family, indicates that GDF-9 is a new member of the family of growth and differentiation factors. Based on the known activities of many of the other members, it can be expected that GDF-9 will also possess biological activities that will make it useful as a diagnostic and therapeutic reagent.

For example, another regulatory protein that has been found to have structural homology with TGF-β is inhibin, a specific and potent polypeptide inhibitor of the pituitary secretion of FSH. Inhibin has been isolated from ovarian follicular fluid. Because of its suppression of FSH, inhibin has potential to be used as a contraceptive in both males and females. GDF-9 may possess similar biological activity since it is also an ovarian specific peptide. Inhibin has also been shown to be useful as a marker for certain ovarian tumors (Lappohn, et al., *N. Engl. J. Med.,* 321:790, 1989). GDF-9 may also be useful as a marker for identifying primary and metastatic neoplasms of ovarian origin. Similarly, GDF-9 may be useful as an indicator of developmental anomalies in prenatal screening procedures.

Another peptide of the TGF-β family is MIS, produced by the testis and responsible for the regression of the Mullerian ducts in the male embryo. MIS has been show to inhibit the growth of human ovarian cancer in nude mice (Donahoe, et al., *Ann. Surg.,* 194:472, 1981). GDF-9 may function similarly and may, therefore, be useful as an anti-cancer agent, such as for the treatment of ovarian cancer.

GDF-9 may also function as a growth stimulatory factor and, therefore, be useful for the survival of various cell populations in vitro. In particular, if GDF-9 plays a role in oocyte maturation, it may be useful in in vitro fertilization procedures, e.g., in enhancing the success rate. Many of the members of the TGF-β family are also important mediators of tissue repair. TGF-β has been shown to have marked effects on the formation of collagen and causes a striking angiogenic response in the newborn mouse (Roberts, et al., *Proc. Natl. Acad. Sci. USA,* 83:4167, 1986). GDF-9 may also have similar activities and may be useful in repair of tissue injury caused by trauma or burns for example.

The term "substantially pure" as used herein refers to GDF-9 which is substantially free of other proteins, lipids, carbohydrates or other materials with which it is naturally associated. One skilled in the art can purify GDF-9 using standard techniques for protein purification. The substantially pure polypeptide will yield a single major band on a non-reducing polyacrylamide gel. The purity of the GDF-9 polypeptide can also be determined by amino-terminal amino acid sequence analysis. GDF-9 polypeptide includes functional fragments of the polypeptide, as long as the activity of GDF-9 remains. Smaller peptides containing the biological activity of GDF-9 are included in the invention.

The invention provides polynucleotides encoding the GDF-9 protein. These polynucleotides include DNA, cDNA and RNA sequences which encode GDF-9. It is understood that all polynucleotides encoding all or a portion of GDF-9 are also included herein, as long as they encode a polypeptide with GDF-9 activity. Such polynucleotides include naturally occurring, synthetic, and intentionally manipulated polynucleotides. For example, GOF-9 polynucleotide may be subjected to site-directed mutagenesis. The polynucleotide sequence for GDF-9 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-9 polypeptide encoded by the nucleotide sequence is functionally unchanged.

Specifically disclosed herein is a cDNA sequence for GDF-9 which is 1712 base pairs in length and contains an open reading frame beginning with a methionine codon at nucleotide 29. The encoded polypeptide is 441 amino acids in length with a molecular weight of about 49.6 kD, as determined by nucleotide sequence analysis. The GDF-9 sequence contains a core of hydrophobic amino acids near the N-terminus, suggestive of a signal sequence for secretion. GDF-9 contains four potential N-glycosylation sites at asparagine residues 163, 229, 258, and 325 and a putative tetrabasic proteolytic processing site (RRRR) at amino acids 303-306. The mature C-terminal fragment of GDF-9 is predicted to be 135 amino acids in length and have an unglycosylated molecular weight of about 15.6 kD, as determined by nucleotide sequence analysis. One skilled in the art can modify, or partially or completely remove the glycosyl groups from the GDF-9 protein using standard techniques. Therefore, the functional protein or fragments thereof of the invention includes glycosylated, partially glycosylated and unglycosylated species of GDF-9.

The degree of sequence identity of GDF-9 with known TGF-β family members ranges from a minimum of 21% with Mullerian inhibiting substance (MIS) to a maximum of 34% with bone morphogenetic protein-4 (BMP-4). GDF-9 specifically disclosed herein differs from the known family members in its pattern of cysteine residues in the C-terminal region. GDF-9 lacks the fourth cysteine of the seven cysteines present in other family members; in place of cysteine at this position, the GDF-9 sequence contains a serine residue. This GDF-9 does not contain a seventh cysteine residue elsewhere in the C-terminal region.

Minor modifications of the recombinant GDF-9 primary amino acid sequence may result in proteins which have substantially equivalent activity as compared to the GDF-9 polypeptide described herein. Such modifications may be deliberate, as by site-directed mutagenesis, or may be spontaneous. All of the polypeptides produced by these modifications are included herein as long as the biological activity of GDF-9 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-9 biological activity.

The nucleotide sequence encoding the GDF-9 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the GDF-9 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

The development of specific DNA sequences encoding GDF-9 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formaton of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for GDF-9 peptides having at least one epitope, using antibodies specific for GDF-9. Such antibodies can be either polyclonally or monoclonally derived and used to detect expression product indicative of the presence of GDF-9 cDNA.

DNA sequences encoding GDF-9 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-9 polynucleotide sequences may be inserted into a recombinant expression vector. The term "recombinant expression vector" refers to a plasmid, virus or other vehicle known in the art that has been manipulated by insertion or incorporation of the GDF-9 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-9 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-9 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-9 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and $F(ab')_2$, which are capable of binding an epitopic determinant on GDF-9.

The term "cell-proliferative disorder" denotes malignant as well as non-malignant cell populations which often appear to differ from the surrounding tissue both morphologically and genotypically. The GDF-9 polynucleotide that is an antisense molecule is useful in treating malignancies of the various organ systems, particularly, for example, the ovaries. Essentially, any disorder which is etiologically linked to altered expression of GDF-9 could be considered susceptible to treatment with a GDF-9 suppressing reagent.

The invention provides a method for detecting a cell proliferative disorder of the ovary which comprises contacting an anti-GDF-9 antibody with a cell suspected of having a GDF-9 associated disorder and detecting binding to the antibody. The antibody reactive with GDF-9 is labeled with a compound which allows detection of binding to GDF-9. For purposes of the invention, an antibody specific for GDF-9 polypeptide may be used to detect the level of GDF-9 in biological fluids and tissues. Any specimen containing a detectable amount of antigen can be used. A preferred sample of this invention is tissue of ovarian origin, specifically tissue containing granulosa cells or ovarian follicular fluid. The level of GDF-9 in the suspect cell can be compared with the level in a normal cell to determine whether the subject has a GDF-9-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utiuized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{53}$Cr, and $^{56}$Fe.

The monoclonal antibodies of the invention can be used in vitro and in vivo to monitor the course of amelioration of a GDF-9-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-9-associated disease is effective. The term "ameliorate" denotes a lessening of the detrimental effect of the GDF-9-associated disease in the subject receiving therapy.

The present invention identifies a nucleotide sequence that can be expressed in an altered manner as compared to expression in a normal cell, therefore, it is possible to design appropriate therapeutic or diagnostic techniques directed to this sequence. Thus, where a cell-proliferative disorder is associated with the expression of GDF-9, nucleic acid sequences that interfere with GDF-9 expression at the translational level can be used. This approach utilizes, for example, antisense nucleic acid and ribozymes to block translation of a specific GDF-9 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-9-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585,1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by GDF-9 protein. Such therapy would achieve its therapeutic effect by introduction of the GDF-9 antisense polynucleotide into cells having the proliferative disorder. Delivery of antisense GDF-9 polynucleotide can be achieved using a recombinant expression vector such as a chimeric virus or a colloidal dispersion system.

Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-9 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GDF-9 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-9 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-9 in the reproductive tract, there are a variety of applications using the polypeptide, polynucleotide and antibodies of the invention, related to contraception, fertility and pregnancy. GDF-9 could play a role in regulation of the menstrual cycle and, therefore, could be useful in various contraceptive regimens.

The following examples are intended to illustrate but not limit the invention. While they are typical of those that might be used, other procedures known to those skilled in the art may alternatively be used.

EXAMPLE 1

IDENTIFICATION AND ISOLATION OF A NOVEL TGF-β FAMILY MEMBER

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual *E. coli* colonies carrying these subcloned inserts, and using a combination of random sequencing and hybridization analysis to eliminate known members of the superfamily.

GDF-9 was identified from a mixture of PCR products obtained with the primers SJL160 (5'-CCGGAATTCGGITGG(G/C/A)A(G/A/T/C)(G/C/A)A(G/

A/T/C) TGG(A/G)TI(A/G)TI(T/G)CICC-3') (SEQUENCE ID NO. 1) and SJL153 (5'-CCGGAATTC(A/G)CAI(G/C)C (A/G)CAIC(T/C)(G/A/T/C)(C/G/T)TIG(T/C)I(G/A)(TC) CAT-3') (SEQUENCE ID NO. 2). PCR using these primers was carried out with 2 μg mouse genomic DNA at 94° C. for 1 min, 50° C. for 2 min, and 72° C. for 2 min for 40 cycles.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL160 and SJL153, yielded three known sequences (inhibin βB, BMP-2, and BMP-4) and one novel sequence (designated GDF-9) among 145 subclones analyzed.

RNA isolation and Northern analysis were carried out as described previously (Lee, S. J., Mol. Endocrinol. 4:1034, 1990). An oligo dT-primed cDNA library was prepared from 2.5–3 μg of ovary poly A-selected RNA in the lambda ZAP II vector according to the instructions provided by Stratagene. The ovary library was not amplified prior to screening. Filters were hybridized as described previously (Lee, S.-J., Proc. Natl. Acad. Sci. USA., 88:4250–4254, 1991). DNA sequencing of both strands was carried out using the dideoxy chain termination method (Sanger, et al., Proc. Natl. Acad. Sci., USA, 74:5463–5467, 1977) and a combination of the S1 nuclease/exonuclease III strategy (Henikoff, S., Gene, 28:351–359, 1984) and synthetic oligonucleotide primers.

EXAMPLE 2

EXPRESSION PATTERN AND SEQUENCE OF GDF-9

Figure 1:
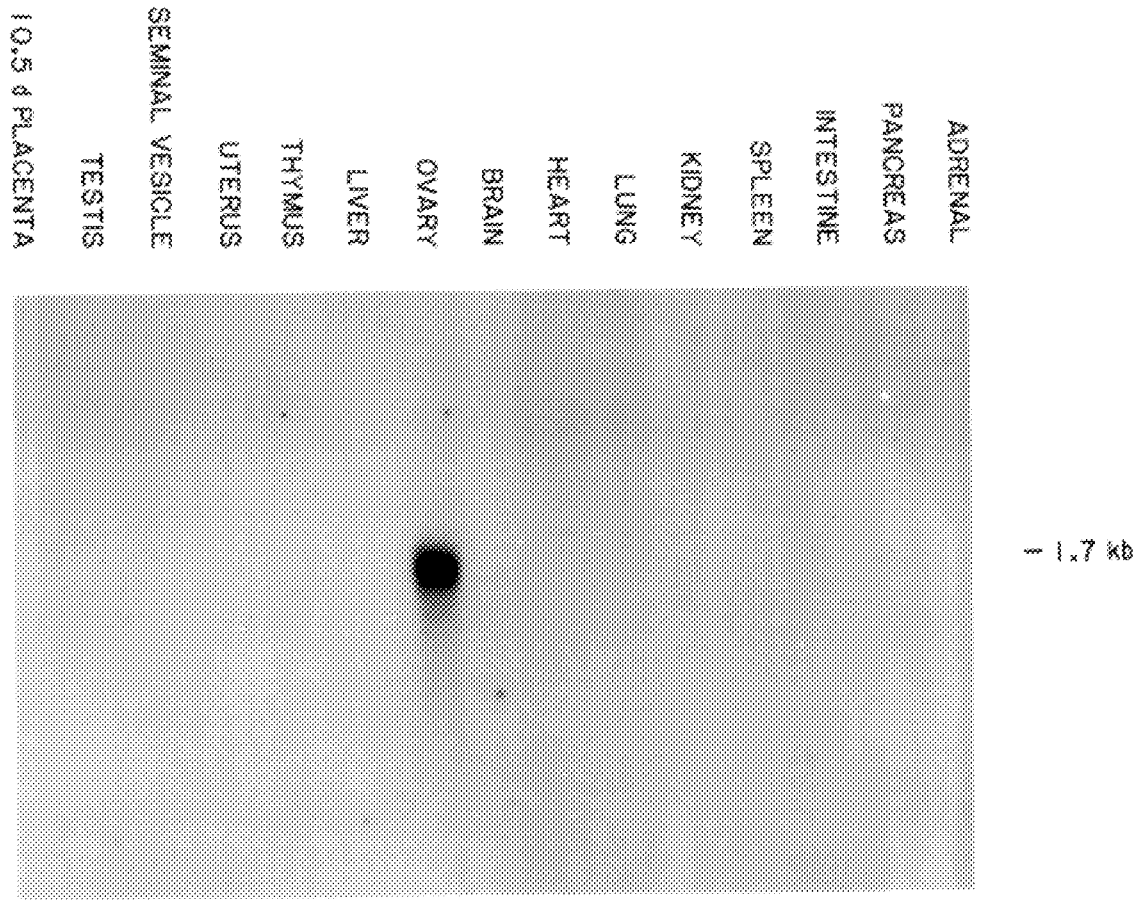
FIG. 1 shows expression of GDF-9 mRNA in adult tissues.

To determine the expression pattern of GDF-9, RNA samples prepared from a variety of adult tissues were screened by Northern analysis. Five micrograms of twice polyA-selected RNA prepared from each tissue were electrophoresed on formaldehyde gels, blotted and probed with GDF-9. As shown in FIG. 1, the GDF-9 probe detected a 1.7 kb mRNA expressed exclusively in the ovary.

A mouse ovary cDNA library of $1.5 \times 10^6$ recombinant phage was constructed in lambda ZAP II and screened with a probe derived from the GDF-9 PCR product. The nucleotide sequence of the longest of nineteen hybridizing clones is shown in FIG. 2. Consensus N-glycosylation signals are denoted by plain boxes. The putative tetrabasic processing sites are denoted by stippled boxes. The in-frame termination codons upstream of the putative initiating ATG and the consensus polyadenylation signals are underlined. The poly A tails are not shown. Numbers indicate nucleotide position relative to the 5' end. The 1712 bp sequence contains a long open reading frame beginning with a methionine codon at nucleotide 29 and potentially encoding a protein 441 amino acids in length with a molecular weight of 49.6 kD. Like other TGF-β family members, the GDF-9 sequence contains a core of hydrophobic amino acids near the N-terminus suggestive of a signal sequence for secretion. GDF-9 contains four potential N-glycosylation sites at asparagine residues 163, 229, 258, and 325 and a putative tetrabasic proteolytic processing site (RRRR) (amino acid residues 303-306 of SEQ ID NO:4) at amino acids 303-306. The mature C-terminal fragment of GDF-9 is predicted to be 135 amino acids in length and have an unglycosylated molecular weight of 15.6 kD.

Although the C-terminal portion of GDF-9 clearly shows homology with the other family members, the sequence of GDF-9 is significantly diverged from those of the other family members (FIGS. 3 and 4). FIG. 3 shows the alignment of the C-terminal sequences of GDF-9 with the corresponding regions of human GDF-1 (Lee, Proc. Natl. Acad. Sci. USA, 88:4250–4254, 1991), Xenopus Vg-1 (Weeks, et al., Cell, 51:861–867, 1987), human Vgr-1 (Celeste, et al., Proc. Natl. Acad. Sci. USA, 87:9843–9847, 1990), human OP-1 (Ozkaynak, et al., EMBO J., 9:2085–2093, 1990), human BMP-5 (Celeste, et al., Proc. Natl. Acad. Sci. USA, 87:9843–9847, 1990), Drosophila 60A (Wharton, et al., Proc. Natl. Acad. Sci. USA, 88:9214–9218, 1991), human BMP-2 and 4 (Wozney, et al., Science, 242:1528–1534, 1988), Drosophila DPP (Padgett, et al., Nature, 325:81–84, 1987), human BMP-3 (Wozney, et al., Science, 242:1528–1534, 1988), human MIS (Cate, et al., Cell, 45:685–698,1986), human inhibin, βA, and βB (Mason, et al., Biochem, Biophys. Res. Commun., 135:957–964, 1986), human TGF-β1 (Derynck, et al., Nature, 316:701–705, 1985), humanTGF-β2 (deMartin, et al., EMBO J., 6:3673–3677, 1987), human TGF-β3 (ten Dijke, et al., Proc. Natl. Acad. Sci. USA, 85:4715–4719, 1988), chicken TGF-β4 (Jakowlew, et al., Mol. Endocrinol., 2:1186–1195, 1988), and Xenopus TGF-β5 (Kondaiah, et al., J. Biol. Chem., 265:1089–1093, 1990). The conserved cysteine residues are shaded. Dashes denote gaps introduced in order to maximize the alignment.

FIG. 4 shows the amino acid homologies among the different members of the TGF-β superfamily. Numbers represent percent amino acid identities between each pair calculated from the first conserved cysteine to the C-terminus. Boxes represent homologies among highly-related members within particular subgroups.

The degree of sequence identify with known family members ranges from a minimum of 21% with MIS to a maximum of 34% with BMP-4. Hence, GDF-9 is comparable to MIS in its degree of sequence divergence from the other members of this superfamily. Moreover, GDF-9 shows no significant sequence homology to other family members in the pro-region of the molecule. GDF-9 also differs from the known family members in its pattern of cysteine residues in the C-terminal region. GDF-9 lacks the fourth cysteine of the seven cysteines that are present in all other family members; in place of cysteine at this position, the GDF-9 sequence contains a serine residue. In addition, GDF-9 does not contain a seventh cysteine residue elsewhere in the C-terminal region.

EXAMPLE 3

IMMUNOCHEMICAL LOCALIZATION OF GDF-9 IN THE ZONA PELLUCIDA

To determine whether GDF-9 mRNA was translated, sections of adult ovaries were incubated with antibodies directed against recombinant GDF-9 protein. In order to raise antibodies against GDF-9, portions of GDF-9 cDNA spanning amino acids 30 to 295 (pro-region) or 308 to 441 (mature region) were cloned into the T7-based pET3 expression vector (provided by F. W. Studier, Brookhaven National Laboratory), and the resulting plasmids were transformed into the BL21 (DE3) bacterial strain. Total cell extracts from isopropyl β-D-thiogalactoside-induced cells were electrophoresed on SDS/polyacrylamide gels, and the GDF-9 protein fragments were excised, mixed with Freund's adjuvant, and used to immunize rabbits by standard methods known to those of skill in the art. All immunizations were carried out by Spring Valley Lab (Sykesville, Md). The presence of GDF-9-reactive antibodies in the sera of these rabbits was assessed by Western analysis of bacterially-expressed protein fragments. The resulting serum was shown to react with the bacterially-expressed protein by Western analysis.

Figure 5A:
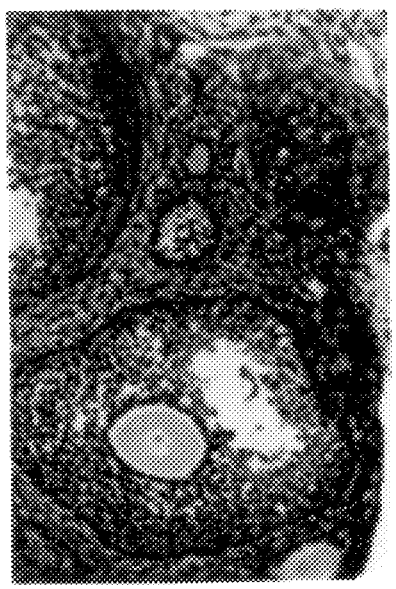
FIG. 5 shows the immunohistochemical localization of GDF-9 protein. Adjacent sections of an adult ovary were either stained with hematoxyiin and eosin (FIG. 5a) or incubated with immune (FIG. 5b) or pre-immune (FIG. 5c) serum at a dilution of 1:500. Anti-GDF-9 antiserum was prepared by expressing the C-terminal portion of murine GDF-9 (residues 308-441) in bacteria, excising GDF-9 protein from preparative SOS gels, and immunizing rabbits. Sites of antibody binding were visualized using the Vectastain ABC kit (Vector Labs).
Figure 5B:
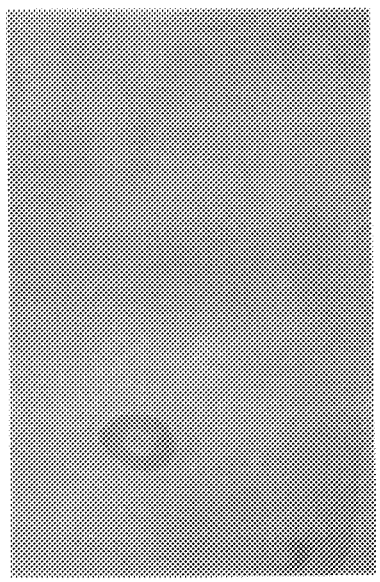
Figure 5C:
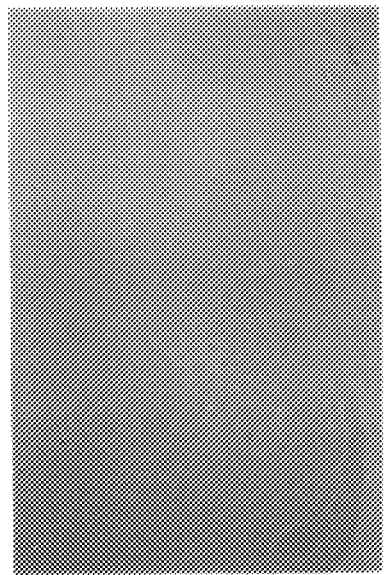

For immunohistochemical studies, ovaries were removed from adult mice, fixed in 4% paraformaidehyde, embedded in paraffin, and sectioned. Sites of antibody binding were detected by using the Vectastain ABC kit, according to the instructions provided by Vector Laboratories. FIG. 5 shows the immunohistochemical localization of GDF-9 protein. Adjacent sections of an adult ovary were either stained with hematoxylin and eosin (FIG. 5a) or incubated with immune (FIG. 5b) or pre-immune (FIG. 5c) serum at a dilution of 1:500. As shown in FIG. 5b, the antiserum detected protein solely in oocytes. No staining was detected using pre-immune serum (FIG. 5c). Hence, GDF-9 protein appears to translated in vivo by oocytes.

EXAMPLE 4

ISOLATION OF HUMAN GDF-9

In order to isolate a cDNA clone encoding human GDF-9, a cDNA library was constructed in lambda ZAP II using poly A-selected RNA prepared from an adult human ovary. From this library, a cDNA clone containing the entire human GDF-9 coding sequence was identified using standard screening techniques as in Example 1 and using the murine GDF-9 clone as a probe. A comparison of the predicted amino acid sequences of murine (top lines) and human (bottom lines) GDF-9 is shown in FIG. 6. Numbers represent amino acid positions relative to the N-termini. Vertical lines represent sequence identities. Dots represent gaps introduced in order to maximize the alignment. The clear box shows the predicted proteolytic processing sites. The shaded boxes show the cysteine residues in the mature region of the proteins. The bars at the bottom show a schematic of the pre-(clear) and mature (shaded) regions of GDF-9 with the percent sequence identities between the murine and human sequences shown below.

Like murine GDF-9, human GDF-9 contains a hydrophobic leader sequence, a putative RXXR proteolytic cleavage site, and a C-terminal region containing the hallmarks of other TGF-β family members. Murine and human GDF-9 are 64% identical in the pro- region and 90% identical in the predicted mature region of the molecule. The high degree of homology between the two sequences suggests that human GDF-9 plays an important role during embryonic development and/or in the adult ovary.

EXAMPLE 5

NUCLEIC ACID DETECTION OF EXPRESSION OF GDF-9 IN OOCYTES

In order to localize the expression of GDF-9 in the ovary, in situ hybridization to mouse ovary sections was carried out using an antisense GDF-9 RNA probe. FIG. 7 shows in situ hybridization to adult ovary sections using a GDF-9 RNA probe. [$^{35}$S]-labeled anti-sense (FIGS. 7a and 7c) or sense (FIGS. 7b and 7d) GDF-9 RNA probes were hybridized to adjacent paraffin-embedded sections of ovaries fixed in 4% paraformaldehyde. Sections were dipped in photographic emulsion, exposed, developed, and then stained with hematoxylin and eosin. Two representative fields are shown.

As shown in FIGS. 7a and 7c, GDF-9 mRNA was detected primarily in oocytes in adult ovaries. Every oocyte (regardless of the stage of follicular development) examined showed GDF-9 expression, and no expression was detected in any other cell types. No hybridization was seen using a control GDF-9 sense RNA probe (FIGS. 7b and 7d). Hence, GDF-9 expression appears to be oocyte-specific in adult ovaries.

To determine the pattern of expression of GDF-9 mRNA during ovarian development, sections of neonatal ovaries were probed with a GDF-9 RNA probe. FIG. 8 shows in situ hybridization to a postnatal day 4 ovary section using an antisense GDF-9 RNA probe. Sections were prepared as described for FIG. 7. Following autoradiography and staining, the section was photographed under bright-field (FIG. 8a) or dark-field (FIG. 8b) illumination.

FIG. 9 shows in situ hybridization to postnatal day 8 ovary sections using an antisense (FIG. 9a) or sense (FIG. 9b) GDF-9 RNA probe. Sections were prepared as described for FIG. 7.

GDF-9 mRNA expression was first detected at the onset of follicular development. This was most clearly evident at postnatal day 4, where only oocytes that were present in follicles showed GDF-9 expression (FIG. 8); no expression was seen in oocytes that were not surrounded by granulosa cells. By postnatal day 8, every oocyte appeared to have undergone follicular development, and every oocyte showed GDF-9 expression (FIG. 9).

To determine whether GDF-9 was also expressed following ovulation, sections of mouse oviducts were examined by in situ hybridization. FIG. 10 shows in situ hybridization to adult oviduct sections using an antisense (FIG. 10a) or sense (FIG. 10b) GDF-9 RNA probe. Sections were prepared as described for FIG. 7.

FIG. 11 shows in situ hybridization to an adult oviduct (0.5 days following fertilization) section using an antisense GDF-9 RNA probe. Sections were prepared as described for FIG. 7. Following autoradiography and staining, the section was photographed under bright-field (FIG. 11a) or dark-field (FIG. 11b) illumination.

As shown in FIG. 10, GDF-9 was expressed by oocytes that had been released into the oviduct. However, the expression of GDF-9 mRNA turned off rapidly following fertilization of the oocytes; by day 0.5 following fertilization, only some embryos (such as the one shown in FIG. 11) expressed GDF-9 mRNA, and by day 1.5, all embryos were negative for GDF-9 expression.

Although the invention has been described with reference to the presently preferred embodiment, it should be understood that various modifications can be made without departing from the spirit of the invention. Accordingly, the invention is limited only by the following claims.

SUMMARY OF SEQUENCES

Sequence ID No. 1 is the nucleotide sequence for the primer, SJL160, for GDF-9 (page 24, lines 15 and 16);

Sequence ID No. 2 is the nucleotide sequence for the primer, SJL153, for GDF-9 (page 24, lines 17 and 18);

Sequence ID No. 3 is the nucleotide and deduced amino acid sequence for GDF-9 (FIG. 2);

Sequence ID No. 4 is the deduced amino acid sequence for GDF-9 (FIG. 2);

Sequence ID No. 5 is the amino acid sequence of the C-terminus of GDF-3 (FIG. 3);

Sequence ID No. 6 is the amino acid sequence of the C-terminus of GDF-9 (FIG. 3);

Sequence ID No. 7 is the amino acid sequence of the C-terminus of GDF-1 (FIG. 3);
Sequence ID No. 8 is the amino acid sequence of the C-terminus of Vg-1 (FIG. 3);
Sequence ID No. 9 is the amino acid sequence of the C-terminus of Vgr-1 (FIG. 3);
Sequence ID No. 10 is the amino acid sequence of the C-terminus of OP-1 (FIG. 3);
Sequence ID No. 11 is the amino acid sequence of the C-terminus of BMP-5 (FIG. 3);
Sequence ID No. 12 is the amino acid sequence of the C-terminus of 60A (FIG. 3);
Sequence ID No. 13 is the amino acid sequence of the C-terminus of BMP-2 (FIG. 3);
Sequence ID No. 14 is the amino acid sequence of the C-terminus of BMP-4 (FIG. 3);
Sequence ID No. 15 is the amino acid sequence of the C-terminus of DPP (FIG. 3);
Sequence ID No. 16 is the amino acid sequence of the C-terminus of BMP-3 (FIG. 3);
Sequence ID No. 17 is the amino acid sequence of the C-terminus of MIS (FIG. 3);
Sequence ID No. 18 is the amino acid sequence of the C-terminus of inhibin α (FIG. 3);
Sequence ID No. 19 is the amino acid sequence of the C-terminus of inhibin βA (FIG. 3);
Sequence ID No. 20 is the amino acid sequence of the C-terminus of inhibin βB (FIG. 3);
Sequence ID No.21 is the amino acid sequence of the C-terminus of TGF-β1 (FIG. 3);
Sequence ID No. 22 is the amino acid sequence of the C-terminus of TGF-β2 (FIG. 3);
Sequence ID No. 23 is the amino acid sequence of the C-terminus of TGF-β3 (FIG. 3);
Sequence ID No. 24 is the amino acid sequence of the C-terminus of TGF-β4 (FIG. 3);
Sequence ID No. 25 is the amino acid sequence of the C-terminus of TGF-β5 (FIG. 3); and
Sequence ID No. 26 is the amino acid sequence of human GDF-9 (FIG. 6).

---

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SJL160

( i x ) FEATURE:
        ( A ) NAME/KEY: CDS
        ( B ) LOCATION: 1..35
        ( D ) OTHER INFORMATION: /note= "Where "B"occurs, B = inosine"

( x i ) SEQUENCE DESCRIPTION: SEQ ID NO:1:

CCGGAATTCG GBTGGVANVA NTGGRTBRTB KCBCC 35

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SJL153

( i x ) FEATURE:
        ( A ) NAME/KEY: CDS
        ( B ) LOCATION: 1..33

( x i ) SEQUENCE DESCRIPTION: SEQ ID NO:2:

CCGGAATTCR CADSCRCADC YNBTDGYDRY CAT 33

( 2 ) INFORMATION FOR SEQ ID NO:3:

( i ) SEQUENCE CHARACTERISTICS:
        ( A ) LENGTH: 1712 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: GDF-9

( i x ) FEATURE:
        ( A ) NAME/KEY: CDS
        ( B ) LOCATION: 29..1351

( x i ) SEQUENCE DESCRIPTION: SEQ ID NO:3:

```
ATGCGTTCCT TCTTAGTTCT TCCAAGTC ATG GCA CTT CCC AGC AAC TTC CTG           52
                              Met Ala Leu Pro Ser Asn Phe Leu
                                1               5

TTG GGG GTT TGC TGC TTT GCC TGG CTG TGT TTT CTT AGT AGC CTT AGC         100
Leu Gly Val Cys Cys Phe Ala Trp Leu Cys Phe Leu Ser Ser Leu Ser
         10              15                  20

TCT CAG GCT TCT ACT GAA GAA TCC CAG AGT GGA GCC AGT GAA AAT GTG         148
Ser Gln Ala Ser Thr Glu Glu Ser Gln Ser Gly Ala Ser Glu Asn Val
 25              30              35                      40

GAG TCT GAG GCA GAC CCC TGG TCC TTG CTG CTG CCT GTA GAT GGG ACT         196
Glu Ser Glu Ala Asp Pro Trp Ser Leu Leu Leu Pro Val Asp Gly Thr
                 45              50                  55

GAC AGG TCT GGC CTC TTG CCC CCC CTC TTT AAG GTT CTA TCT GAT AGG         244
Asp Arg Ser Gly Leu Leu Pro Pro Leu Phe Lys Val Leu Ser Asp Arg
             60                  65                  70

CGA GGT GAG ACC CCT AAG CTG CAG CCT GAC TCC AGA GCA CTC TAC TAC         292
Arg Gly Glu Thr Pro Lys Leu Gln Pro Asp Ser Arg Ala Leu Tyr Tyr
         75                  80              85

ATG AAA AAG CTC TAT AAG ACG TAT GCT ACC AAA GAG GGG GTT CCC AAA         340
Met Lys Lys Leu Tyr Lys Thr Tyr Ala Thr Lys Glu Gly Val Pro Lys
         90              95                 100

CCC AGC AGA AGT CAC CTC TAC AAT ACC GTC CGG CTC TTC AGT CCC TGT         388
Pro Ser Arg Ser His Leu Tyr Asn Thr Val Arg Leu Phe Ser Pro Cys
105              110                 115                 120

GCC CAG CAA GAG CAG GCA CCC AGC AAC CAG GTG ACA GGA CCG CTG CCG         436
Ala Gln Gln Glu Gln Ala Pro Ser Asn Gln Val Thr Gly Pro Leu Pro
                125                 130                 135

ATG GTG GAC CTG CTG TTT AAC CTG GAC CGG GTG ACT GCC ATG GAA CAC         484
Met Val Asp Leu Leu Phe Asn Leu Asp Arg Val Thr Ala Met Glu His
             140                 145                 150

TTG CTC AAA TCG GTC TTG CTA TAC ACT CTG AAC AAC TCT GCC TCT TCC         532
Leu Leu Lys Ser Val Leu Leu Tyr Thr Leu Asn Asn Ser Ala Ser Ser
         155                 160                 165

TCC TCC ACT GTG ACC TGT ATG TGT GAC CTT GTG GTA AAG GAG GCC ATG         580
Ser Ser Thr Val Thr Cys Met Cys Asp Leu Val Val Lys Glu Ala Met
170             175                 180

TCT TCT GGC AGG GCA CCC CCA AGA GCA CCG TAC TCA TTC ACC CTG AAG         628
Ser Ser Gly Arg Ala Pro Pro Arg Ala Pro Tyr Ser Phe Thr Leu Lys
185             190                 195                 200

AAA CAC AGA TGG ATT GAG ATT GAT GTG ACC TCC CTC CTT CAG CCC CTA         676
Lys His Arg Trp Ile Glu Ile Asp Val Thr Ser Leu Leu Gln Pro Leu
                205                 210                 215

GTG ACC TCC AGC GAG AGG AGC ATT CAC CTG TCT GTC AAT TTT ACA TGC         724
Val Thr Ser Ser Glu Arg Ser Ile His Leu Ser Val Asn Phe Thr Cys
             220                 225                 230

ACA AAA GAC CAG GTG CCA GAG GAC GGA GTG TTT AGC ATG CCT CTC TCA         772
```

```
Thr  Lys  Asp  Gln  Val  Pro  Glu  Asp  Gly  Val  Phe  Ser  Met  Pro  Leu  Ser
          235                      240                     245

GTG  CCT  CCT  TCC  CTC  ATC  TTG  TAT  CTC  AAC  GAC  ACA  AGC  ACC  CAG  GCC       820
Val  Pro  Pro  Ser  Leu  Ile  Leu  Tyr  Leu  Asn  Asp  Thr  Ser  Thr  Gln  Ala
     250                      255                     260

TAC  CAC  TCT  TGG  CAG  TCT  CTT  CAG  TCC  ACC  TGG  AGG  CCT  TTA  CAG  CAT       868
Tyr  His  Ser  Trp  Gln  Ser  Leu  Gln  Ser  Thr  Trp  Arg  Pro  Leu  Gln  His
265                      270                     275                      280

CCC  GGC  CAG  GCC  GGT  GTG  GCT  GCC  CGT  CCC  GTG  AAA  GAG  GAA  GCT  ACT       916
Pro  Gly  Gln  Ala  Gly  Val  Ala  Ala  Arg  Pro  Val  Lys  Glu  Glu  Ala  Thr
               285                     290                      295

GAG  GTG  GAA  AGA  TCT  CCC  CGG  CGC  CGT  CGA  GGG  CAG  AAA  GCC  ATC  CGC       964
Glu  Val  Glu  Arg  Ser  Pro  Arg  Arg  Arg  Arg  Gly  Gln  Lys  Ala  Ile  Arg
               300                     305                      310

TCC  GAA  GCG  AAG  GGG  CCA  CTT  CTT  ACA  GCA  TCC  TTC  AAC  CTC  AGC  GAA      1012
Ser  Glu  Ala  Lys  Gly  Pro  Leu  Leu  Thr  Ala  Ser  Phe  Asn  Leu  Ser  Glu
               315                     320                      325

TAC  TTC  AAA  CAG  TTT  CTT  TTC  CCC  CAA  AAC  GAG  TGT  GAA  CTC  CAT  GAC      1060
Tyr  Phe  Lys  Gln  Phe  Leu  Phe  Pro  Gln  Asn  Glu  Cys  Glu  Leu  His  Asp
     330                      335                     340

TTC  AGA  CTG  AGT  TTT  AGT  CAG  CTC  AAA  TGG  GAC  AAC  TGG  ATC  GTG  GCC      1108
Phe  Arg  Leu  Ser  Phe  Ser  Gln  Leu  Lys  Trp  Asp  Asn  Trp  Ile  Val  Ala
345                      350                     355                      360

CCG  CAC  AGG  TAC  AAC  CCT  AGG  TAC  TGT  AAA  GGG  GAC  TGT  CCT  AGG  GCG      1156
Pro  His  Arg  Tyr  Asn  Pro  Arg  Tyr  Cys  Lys  Gly  Asp  Cys  Pro  Arg  Ala
                    365                     370                      375

GTC  AGG  CAT  CGG  TAT  GGC  TCT  CCT  GTG  CAC  ACC  ATG  GTC  CAG  AAT  ATA      1204
Val  Arg  His  Arg  Tyr  Gly  Ser  Pro  Val  His  Thr  Met  Val  Gln  Asn  Ile
               380                     385                      390

ATC  TAT  GAG  AAG  CTG  GAC  CCT  TCA  GTG  CCA  AGG  CCT  TCG  TGT  GTG  CCG      1252
Ile  Tyr  Glu  Lys  Leu  Asp  Pro  Ser  Val  Pro  Arg  Pro  Ser  Cys  Val  Pro
          395                      400                     405

GGC  AAG  TAC  AGC  CCC  CTG  AGT  GTG  TTG  ACC  ATT  GAA  CCC  GAC  GGC  TCC      1300
Gly  Lys  Tyr  Ser  Pro  Leu  Ser  Val  Leu  Thr  Ile  Glu  Pro  Asp  Gly  Ser
     410                      415                     420

ATC  GCT  TAC  AAA  GAG  TAC  GAA  GAC  ATG  ATA  GCT  ACG  AGG  TGC  ACC  TGT      1348
Ile  Ala  Tyr  Lys  Glu  Tyr  Glu  Asp  Met  Ile  Ala  Thr  Arg  Cys  Thr  Cys
425                      430                     435                      440

CGT  TAGCATGGGG  GCCACTTCAA  CAAGCCTGCC  TGGCAGAGCA  ATGCTGTGGG                      1401
Arg

CCTTAGAGTG  CCTGGGCAGA  GAGCTTCCTG  TGACCAGTCT  CTCCGTGCTG  CTCAGTGCAC              1461

ACTGTGTGAG  CGGGGGAAGT  GTGTGTGTGT  GGATGAGCAC  ATCGAGTGCA  GTGTCCGTAG              1521

GTGTAAAGGG  CACACTCACT  GGTCGTTGCC  ATAAACCAAG  TGAAATGTAA  CTCATTTGGA              1581

GAGCTCTTTC  TCCCCACGAG  TGTAGTTTTC  AGTGGACAGA  TTTGTTAGCA  TAAGTCTCGA              1641

GTAGAATGTA  GCTGTGAACA  TGTCAGAGTG  CTGTGGTTTT  ATGTGACGGA  AGAATAAACT              1701

GTTGATGGCA  T                                                                       1712
```

( 2 ) INFORMATION FOR SEQ ID NO:4:

( i ) SEQUENCE CHARACTERISTICS:
        ( A ) LENGTH: 441 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Leu  Pro  Ser  Asn  Phe  Leu  Leu  Gly  Val  Cys  Cys  Phe  Ala  Trp
 1              5                        10                      15
```

-continued

| | | | | | | | | | | | | | |
|---|---|---|---|---|---|---|---|---|---|---|---|---|---|
|Leu|Cys|Phe|Leu|Ser|Ser|Leu|Ser|Ser|Gln|Ala|Ser|Thr|Glu|Glu|Ser|
| | | |20| | |25| | | |30| | | |
|Gln|Ser|Gly|Ala|Ser|Glu|Asn|Val|Glu|Ser|Glu|Ala|Asp|Pro|Trp|Ser|
| | |35| | |40| | | |45| | | | |
|Leu|Leu|Leu|Pro|Val|Asp|Gly|Thr|Asp|Arg|Ser|Gly|Leu|Leu|Pro|Pro|
| |50| | | |55| | | |60| | | | |
|Leu|Phe|Lys|Val|Leu|Ser|Asp|Arg|Arg|Gly|Thr|Pro|Lys|Leu|Gln|
|65| | | |70| | | |75| | | |80|
|Pro|Asp|Ser|Arg|Ala|Leu|Tyr|Tyr|Met|Lys|Lys|Leu|Tyr|Lys|Thr|Tyr|
| | | |85| | | |90| | | |95| |
|Ala|Thr|Lys|Glu|Gly|Val|Pro|Lys|Pro|Ser|Arg|Ser|His|Leu|Tyr|Asn|
| | |100| | |105| | | |110| | |
|Thr|Val|Arg|Leu|Phe|Ser|Pro|Cys|Ala|Gln|Gln|Glu|Gln|Ala|Pro|Ser|
| |115| | | |120| | | |125| | |
|Asn|Gln|Val|Thr|Gly|Pro|Leu|Pro|Met|Val|Asp|Leu|Leu|Phe|Asn|Leu|
| |130| | | |135| | | |140| | |
|Asp|Arg|Val|Thr|Ala|Met|Glu|His|Leu|Leu|Lys|Ser|Val|Leu|Leu|Tyr|
|145| | | |150| | | |155| | | |160|
|Thr|Leu|Asn|Asn|Ser|Ala|Ser|Ser|Ser|Thr|Val|Thr|Cys|Met|Cys|
| | | |165| | | |170| | | |175|
|Asp|Leu|Val|Val|Lys|Glu|Ala|Met|Ser|Ser|Gly|Arg|Ala|Pro|Pro|Arg|
| | |180| | | |185| | | |190| |
|Ala|Pro|Tyr|Ser|Phe|Thr|Leu|Lys|Lys|His|Arg|Trp|Ile|Glu|Ile|Asp|
| | |195| | | |200| | | |205| |
|Val|Thr|Ser|Leu|Leu|Gln|Pro|Leu|Val|Thr|Ser|Ser|Glu|Arg|Ser|Ile|
| |210| | | |215| | | |220| | |
|His|Leu|Ser|Val|Asn|Phe|Thr|Cys|Thr|Lys|Asp|Gln|Val|Pro|Glu|Asp|
|225| | | |230| | | |235| | | |240|
|Gly|Val|Phe|Ser|Met|Pro|Leu|Ser|Val|Pro|Pro|Ser|Leu|Ile|Leu|Tyr|
| | | |245| | | |250| | | |255|
|Leu|Asn|Asp|Thr|Ser|Thr|Gln|Ala|Tyr|His|Ser|Trp|Gln|Ser|Leu|Gln|
| | | |260| | | |265| | | |270|
|Ser|Thr|Trp|Arg|Pro|Leu|Gln|His|Pro|Gly|Gln|Ala|Gly|Val|Ala|Ala|
| | |275| | | |280| | | |285| |
|Arg|Pro|Val|Lys|Glu|Glu|Ala|Thr|Glu|Val|Glu|Arg|Ser|Pro|Arg|Arg|
|290| | | |295| | | |300| | | |
|Arg|Arg|Gly|Gln|Lys|Ala|Ile|Arg|Ser|Glu|Ala|Lys|Gly|Pro|Leu|Leu|
|305| | | |310| | | |315| | | |320|
|Thr|Ala|Ser|Phe|Asn|Leu|Ser|Glu|Tyr|Phe|Lys|Gln|Phe|Leu|Phe|Pro|
| | | |325| | | |330| | | |335|
|Gln|Asn|Glu|Cys|Glu|Leu|His|Asp|Phe|Arg|Leu|Ser|Phe|Ser|Gln|Leu|
| | | |340| | | |345| | | |350|
|Lys|Trp|Asp|Asn|Trp|Ile|Val|Ala|Pro|His|Arg|Tyr|Asn|Pro|Arg|Tyr|
| | |355| | | |360| | | |365| |
|Cys|Lys|Gly|Asp|Cys|Pro|Arg|Ala|Val|Arg|His|Arg|Tyr|Gly|Ser|Pro|
| |370| | | |375| | | |380| | |
|Val|His|Thr|Met|Val|Gln|Asn|Ile|Ile|Tyr|Glu|Lys|Leu|Asp|Pro|Ser|
|385| | | |390| | | |395| | | |400|
|Val|Pro|Arg|Pro|Ser|Cys|Val|Pro|Gly|Lys|Tyr|Ser|Pro|Leu|Ser|Val|
| | | |405| | | |410| | | |415|
|Leu|Thr|Ile|Glu|Pro|Asp|Gly|Ser|Ile|Ala|Tyr|Lys|Glu|Tyr|Glu|Asp|
| | | |420| | | |425| | | |430|
|Met|Ile|Ala|Thr|Arg|Cys|Thr|Cys|Arg|

(2) INFORMATION FOR SEQ ID NO:5:

(i) SEQUENCE CHARACTERISTICS:
(A) LENGTH: 117 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: GDF-3

(ix) FEATURE:
(A) NAME/KEY: Protein
(B) LOCATION: 1..117

(xi) SEQUENCE DESCRIPTION: SEQ ID NO:5:

```
Lys Arg Arg Ala Ala Ile Ser Val Pro Lys Gly Phe Cys Arg Asn Phe
1               5                   10                  15
Cys His Arg His Gln Leu Phe Ile Asn Phe Gln Asp Leu Gly Trp His
            20                  25                  30
Lys Trp Val Ile Ala Pro Lys Gly Phe Met Ala Asn Tyr Cys His Gly
        35                  40                  45
Glu Cys Pro Phe Ser Met Thr Thr Tyr Leu Asn Ser Ser Asn Tyr Ala
50                  55                  60
Phe Met Gln Ala Leu Met His Met Ala Asp Pro Lys Val Pro Lys Ala
65                  70                  75                  80
Val Cys Val Pro Thr Lys Leu Ser Pro Ile Ser Met Leu Tyr Gln Asp
                85                  90                  95
Ser Asp Lys Asn Val Ile Leu Arg His Tyr Glu Asp Met Val Val Asp
            100                 105                 110
Glu Cys Gly Cys Gly
            115
```

(2) INFORMATION FOR SEQ ID NO:6:

(i) SEQUENCE CHARACTERISTICS:
(A) LENGTH: 118 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: GDF-9

(ix) FEATURE:
(A) NAME/KEY: Protein
(B) LOCATION: 1..118

(xi) SEQUENCE DESCRIPTION: SEQ ID NO:6:

```
Phe Asn Leu Ser Glu Tyr Phe Lys Gln Phe Leu Phe Pro Gln Asn Glu
1               5                   10                  15
Cys Glu Leu His Asp Phe Arg Leu Ser Phe Ser Gln Leu Lys Trp Asp
            20                  25                  30
Asn Trp Ile Val Ala Pro His Arg Tyr Asn Pro Arg Tyr Cys Lys Gly
        35                  40                  45
Asp Cys Pro Arg Ala Val Arg His Arg Tyr Gly Ser Pro Val His Thr
        50                  55                  60
Met Val Gln Asn Ile Ile Tyr Glu Lys Leu Asp Pro Ser Val Pro Arg
65                  70                  75                  80
```

```
              Pro   Ser   Cys   Val   Pro   Gly   Lys   Tyr   Ser   Pro   Leu   Ser   Val   Leu   Thr   Ile
                                 8 5                             9 0                             9 5

Glu   Pro   Asp   Gly   Ser   Ile   Ala   Tyr   Lys   Glu   Tyr   Glu   Asp   Met   Ile   Ala
                                1 0 0                           1 0 5                           1 1 0

Thr   Arg   Cys   Thr   Cys   Arg
                                1 1 5
```

( 2 ) INFORMATION FOR SEQ ID NO:7:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: GDF-1

( i x ) FEATURE:
        ( A ) NAME/KEY: Protein
        ( B ) LOCATION: 1..122

( x i ) SEQUENCE DESCRIPTION: SEQ ID NO:7:

```
              Pro   Arg   Arg   Asp   Ala   Glu   Pro   Val   Leu   Gly   Gly   Gly   Pro   Gly   Gly   Ala
              1                       5                            1 0                           1 5

Cys   Arg   Ala   Arg   Arg   Leu   Tyr   Val   Ser   Phe   Arg   Glu   Val   Gly   Trp   His
                                2 0                            2 5                            3 0

Arg   Trp   Val   Ile   Ala   Pro   Arg   Gly   Phe   Leu   Ala   Asn   Tyr   Cys   Gln   Gly
                                3 5                            4 0                            4 5

Gln   Cys   Ala   Leu   Pro   Val   Ala   Leu   Ser   Gly   Ser   Gly   Gly   Pro   Pro   Ala
                     5 0                            5 5                            6 0

Leu   Asn   His   Ala   Val   Leu   Arg   Ala   Leu   Met   His   Ala   Ala   Ala   Pro   Gly
              6 5                            7 0                            7 5                            8 0

Ala   Ala   Asp   Leu   Pro   Cys   Cys   Val   Pro   Ala   Arg   Leu   Ser   Pro   Ile   Ser
                                8 5                            9 0                            9 5

Val   Leu   Phe   Phe   Asp   Asn   Ser   Asp   Asn   Val   Val   Leu   Arg   Gln   Tyr   Glu
                                1 0 0                          1 0 5                          1 1 0

Asp   Met   Val   Val   Asp   Glu   Cys   Gly   Cys   Arg
                                1 1 5                          1 2 0
```

( 2 ) INFORMATION FOR SEQ ID NO:8:

( i ) SEQUENCE CHARACTERISTICS:
        ( A ) LENGTH: 118 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Vg-1

( i x ) FEATURE:
        ( A ) NAME/KEY: Protein
        ( B ) LOCATION: 1..118

( x i ) SEQUENCE DESCRIPTION: SEQ ID NO:8:

```
              Arg   Arg   Lys   Arg   Ser   Tyr   Ser   Lys   Leu   Pro   Phe   Thr   Ala   Ser   Asn   Ile
              1                       5                            1 0                           1 5

Cys   Lys   Lys   Arg   His   Leu   Tyr   Val   Glu   Phe   Lys   Asp   Val   Gly   Trp   Gln
                                2 0                            2 5                            3 0
```

```
Asn Trp Val Ile Ala Pro Gln Gly Tyr Met Ala Asn Tyr Cys Tyr Gly
        35              40              45

Glu Cys Pro Tyr Pro Leu Thr Glu Ile Leu Asn Gly Ser Asn His Ala
        50              55              60

Ile Leu Gln Thr Leu Val His Ser Ile Glu Pro Glu Asp Ile Pro Leu
65              70              75              80

Pro Cys Cys Val Pro Thr Lys Met Ser Pro Ile Ser Met Leu Phe Tyr
                85              90              95

Asp Asn Asn Asp Asn Val Val Leu Arg His Tyr Glu Asn Met Ala Val
            100             105             110

Asp Glu Cys Gly Cys Arg
            115
```

(2) INFORMATION FOR SEQ ID NO:9:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Vgr-1

(ix) FEATURE:
        (A) NAME/KEY: Protein
        (B) LOCATION: 1..118

(xi) SEQUENCE DESCRIPTION: SEQ ID NO:9:

```
Arg Val Ser Ser Ala Ser Asp Tyr Asn Ser Ser Glu Leu Lys Thr Ala
1               5               10              15

Cys Arg Lys His Glu Leu Tyr Val Ser Phe Gln Asp Leu Gly Trp Gln
        20              25              30

Asp Trp Ile Ile Ala Pro Lys Gly Tyr Ala Ala Asn Tyr Cys Asp Gly
        35              40              45

Glu Cys Ser Phe Pro Leu Asn Ala His Met Asn Ala Thr Asn His Ala
        50              55              60

Ile Val Gln Thr Leu Val His Leu Met Asn Pro Glu Tyr Val Pro Lys
65              70              75              80

Pro Cys Cys Ala Pro Thr Lys Leu Asn Ala Ile Ser Val Leu Tyr Phe
                85              90              95

Asp Asp Asn Ser Asn Val Ile Leu Lys Lys Tyr Arg Asn Met Val Val
            100             105             110

Arg Ala Cys Gly Cys His
            115
```

(2) INFORMATION FOR SEQ ID NO:10:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: OP-1

(ix) FEATURE:
        (A) NAME/KEY: Protein
        (B) LOCATION: 1..118

( x i ) SEQUENCE DESCRIPTION: SEQ ID NO:10:

| Arg<br>1 | Met | Ala | Asn | Val<br>5 | Ala | Glu | Asn | Ser | Ser<br>10 | Ser | Asp | Gln | Arg | Gln<br>15 | Ala |

| Cys | Lys | Lys | His<br>20 | Glu | Leu | Tyr | Val | Ser<br>25 | Phe | Arg | Asp | Leu | Gly<br>30 | Trp | Gln |

| Asp | Trp | Ile<br>35 | Ile | Ala | Pro | Glu | Gly<br>40 | Tyr | Ala | Ala | Tyr | Tyr<br>45 | Cys | Glu | Gly |

| Glu | Cys<br>50 | Ala | Phe | Pro | Leu | Asn<br>55 | Ser | Tyr | Met | Asn | Ala<br>60 | Thr | Asn | His | Ala |

| Ile<br>65 | Val | Gln | Thr | Leu | Val<br>70 | His | Phe | Ile | Asn | Pro<br>75 | Glu | Thr | Val | Pro | Lys<br>80 |

| Pro | Cys | Cys | Ala | Pro<br>85 | Thr | Gln | Leu | Asn | Ala<br>90 | Ile | Ser | Val | Leu | Tyr<br>95 | Phe |

| Asp | Asp | Ser | Ser<br>100 | Asn | Val | Ile | Leu | Lys<br>105 | Lys | Tyr | Arg | Asn | Met<br>110 | Val | Val |

| Arg | Ala | Cys | Gly | Cys | His |
| | | 115 | | | |

( 2 ) INFORMATION FOR SEQ ID NO:11:

( i ) SEQUENCE CHARACTERISTICS:
        ( A ) LENGTH: 118 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: BMP-5

( i x ) FEATURE:
        ( A ) NAME/KEY: Protein
        ( B ) LOCATION: 1..118

( x i ) SEQUENCE DESCRIPTION: SEQ ID NO:11:

| Arg<br>1 | Met | Ser | Ser | Val<br>5 | Gly | Asp | Tyr | Asn | Thr<br>10 | Ser | Glu | Gln | Lys | Gln<br>15 | Ala |

| Cys | Lys | Lys | His<br>20 | Glu | Leu | Tyr | Val | Ser<br>25 | Phe | Arg | Asp | Leu | Gly<br>30 | Trp | Gln |

| Asp | Trp | Ile<br>35 | Ile | Ala | Pro | Glu | Gly<br>40 | Tyr | Ala | Ala | Phe | Tyr<br>45 | Cys | Asp | Gly |

| Glu | Cys<br>50 | Ser | Phe | Pro | Leu | Asn<br>55 | Ala | His | Met | Asn | Ala<br>60 | Thr | Asn | His | Ala |

| Ile<br>65 | Val | Gln | Thr | Leu | Val<br>70 | His | Leu | Met | Phe | Pro<br>75 | Asp | His | Val | Pro | Lys<br>80 |

| Pro | Cys | Cys | Ala | Pro<br>85 | Thr | Lys | Leu | Asn | Ala<br>90 | Ile | Ser | Val | Leu | Tyr<br>95 | Phe |

| Asp | Asp | Ser | Ser<br>100 | Asn | Val | Ile | Leu | Lys<br>105 | Lys | Tyr | Arg | Asn | Met<br>110 | Val | Val |

| Arg | Ser | Cys | Gly | Cys | His |
| | | 115 | | | |

( 2 ) INFORMATION FOR SEQ ID NO:12:

( i ) SEQUENCE CHARACTERISTICS:
        ( A ) LENGTH: 118 amino acids
        ( B ) TYPE: amino acid
        ( C ) STRANDEDNESS: single
        ( D ) TOPOLOGY: linear ( i i ) MOLECULE TYPE: protein (v i i) IMMEDIATE SOURCE:
 (B) CLONE: 60A (i x) FEATURE:
 (A) NAME/KEY: Protein
 (B) LOCATION: 1..118

(x i) SEQUENCE DESCRIPTION: SEQ ID NO:12:

| Ser | Pro | Asn | Asn | Val | Pro | Leu | Leu | Glu | Pro | Met | Glu | Ser | Thr | Arg | Ser |
|---|---|---|---|---|---|---|---|---|---|---|---|---|---|---|---|
| 1 | | | | 5 | | | | | 10 | | | | | 15 | |
| Cys | Gln | Met | Gln | Thr | Leu | Tyr | Ile | Asp | Phe | Lys | Asp | Leu | Gly | Trp | His |
| | | | 20 | | | | | 25 | | | | | 30 | | |
| Asp | Trp | Ile | Ile | Ala | Pro | Glu | Gly | Tyr | Gly | Ala | Phe | Tyr | Cys | Ser | Gly |
| | | | 35 | | | | 40 | | | | | 45 | | | |
| Glu | Cys | Asn | Phe | Pro | Leu | Asn | Ala | His | Met | Asn | Ala | Thr | Asn | His | Ala |
| | | 50 | | | | 55 | | | | | 60 | | | | |
| Ile | Val | Gln | Thr | Leu | Val | His | Leu | Leu | Glu | Pro | Lys | Lys | Val | Pro | Lys |
| 65 | | | | | 70 | | | | | 75 | | | | | 80 |
| Pro | Cys | Cys | Ala | Pro | Thr | Arg | Leu | Gly | Ala | Leu | Pro | Val | Leu | Tyr | His |
| | | | | 85 | | | | | 90 | | | | | 95 | |
| Leu | Asn | Asp | Glu | Asn | Val | Asn | Leu | Lys | Lys | Tyr | Arg | Asn | Met | Ile | Val |
| | | | | 100 | | | | | 105 | | | | | 110 | |
| Lys | Ser | Cys | Gly | Cys | His | | | | | | | | | | |
| | | | 115 | | | | | | | | | | | | |

(2) INFORMATION FOR SEQ ID NO:13:

(i) SEQUENCE CHARACTERISTICS:
  (A) LENGTH: 117 amino acids
  (B) TYPE: amino acid
  (C) STRANDEDNESS: single
  (D) TOPOLOGY: linear (i i) MOLECULE TYPE: protein (v i i) IMMEDIATE SOURCE:
  (B) CLONE: BMP-2

(i x) FEATURE:
  (A) NAME/KEY: Protein
  (B) LOCATION: 1..117

(x i) SEQUENCE DESCRIPTION: SEQ ID NO:13:

| Glu | Lys | Arg | Gln | Ala | Lys | His | Lys | Gln | Arg | Lys | Arg | Leu | Lys | Ser | Ser |
|---|---|---|---|---|---|---|---|---|---|---|---|---|---|---|---|
| 1 | | | | 5 | | | | | 10 | | | | | 15 | |
| Cys | Lys | Arg | His | Pro | Leu | Tyr | Val | Asp | Phe | Ser | Asp | Val | Gly | Trp | Asn |
| | | | 20 | | | | | 25 | | | | | 30 | | |
| Asp | Trp | Ile | Val | Ala | Pro | Pro | Gly | Tyr | His | Ala | Phe | Tyr | Cys | His | Gly |
| | | | 35 | | | | | 40 | | | | | 45 | | |
| Glu | Cys | Pro | Phe | Pro | Leu | Ala | Asp | His | Leu | Asn | Ser | Thr | Asn | His | Ala |
| | | 50 | | | | 55 | | | | | 60 | | | | |
| Ile | Val | Gln | Thr | Leu | Val | Asn | Ser | Val | Asn | Ser | Lys | Ile | Pro | Lys | Ala |
| 65 | | | | | 70 | | | | | 75 | | | | | 80 |
| Cys | Cys | Val | Pro | Thr | Glu | Leu | Ser | Ala | Ile | Ser | Met | Leu | Tyr | Leu | Asp |
| | | | | 85 | | | | | 90 | | | | | 95 | |
| Glu | Asn | Glu | Lys | Val | Val | Leu | Lys | Asn | Tyr | Gln | Asp | Met | Val | Val | Glu |
| | | | | 100 | | | | | 105 | | | | | 110 | |
| Gly | Cys | Gly | Cys | Arg | | | | | | | | | | | |
| | | | 115 | | | | | | | | | | | | |

(2) INFORMATION FOR SEQ ID NO:14:

( i ) SEQUENCE CHARACTERISTICS:
  ( A ) LENGTH: 117 amino acids
  ( B ) TYPE: amino acid
  ( C ) STRANDEDNESS: single
  ( D ) TOPOLOGY: linear ( i i ) MOLECULE TYPE: protein ( v i i ) IMMEDIATE SOURCE:
  ( B ) CLONE: BMP-4

( i x ) FEATURE:
  ( A ) NAME/KEY: Protein
  ( B ) LOCATION: 1..117

( x i ) SEQUENCE DESCRIPTION: SEQ ID NO:14:

| Arg | Ser | Pro | Lys | His | His | Ser | Gln | Arg | Ala | Arg | Lys | Lys | Asn | Lys | Asn |
|---|---|---|---|---|---|---|---|---|---|---|---|---|---|---|---|
| 1 | | | | 5 | | | | | 10 | | | | | 15 | |
| Cys | Arg | Arg | His | Ser | Leu | Tyr | Val | Asp | Phe | Ser | Asp | Val | Gly | Trp | Asn |
| | | | 20 | | | | | 25 | | | | | 30 | | |
| Asp | Trp | Ile | Val | Ala | Pro | Pro | Gly | Tyr | Gln | Ala | Phe | Tyr | Cys | His | Gly |
| | | 35 | | | | | 40 | | | | | 45 | | | |
| Asp | Cys | Pro | Phe | Pro | Leu | Ala | Asp | His | Leu | Asn | Ser | Thr | Asn | His | Ala |
| | 50 | | | | | 55 | | | | | 60 | | | | |
| Ile | Val | Gln | Thr | Leu | Val | Asn | Ser | Val | Asn | Ser | Ser | Ile | Pro | Lys | Ala |
| 65 | | | | | 70 | | | | | 75 | | | | | 80 |
| Cys | Cys | Val | Pro | Thr | Glu | Leu | Ser | Ala | Ile | Ser | Met | Leu | Tyr | Leu | Asp |
| | | | | 85 | | | | | 90 | | | | | 95 | |
| Glu | Tyr | Asp | Lys | Val | Val | Leu | Lys | Asn | Tyr | Gln | Glu | Met | Val | Val | Glu |
| | | | 100 | | | | | 105 | | | | | 110 | | |
| Gly | Cys | Gly | Cys | Arg | | | | | | | | | | | |
| | | | | 115 | | | | | | | | | | | |

( 2 ) INFORMATION FOR SEQ ID NO:15:

( i ) SEQUENCE CHARACTERISTICS:
  ( A ) LENGTH: 118 amino acids
  ( B ) TYPE: amino acid
  ( C ) STRANDEDNESS: single
  ( D ) TOPOLOGY: linear ( i i ) MOLECULE TYPE: protein ( v i i ) IMMEDIATE SOURCE:
  ( B ) CLONE: DPP ( i x ) FEATURE:
  ( A ) NAME/KEY: Protein
  ( B ) LOCATION: 1..118

( x i ) SEQUENCE DESCRIPTION: SEQ ID NO:15:

| Lys | Arg | His | Ala | Arg | Arg | Pro | Thr | Arg | Arg | Lys | Asn | His | Asp | Asp | Thr |
|---|---|---|---|---|---|---|---|---|---|---|---|---|---|---|---|
| 1 | | | | 5 | | | | | 10 | | | | | 15 | |
| Cys | Arg | Arg | His | Ser | Leu | Tyr | Val | Asp | Phe | Ser | Asp | Val | Gly | Trp | Asp |
| | | | 20 | | | | | 25 | | | | | 30 | | |
| Asp | Trp | Ile | Val | Ala | Pro | Leu | Gly | Tyr | Asp | Ala | Tyr | Tyr | Cys | His | Gly |
| | | 35 | | | | | 40 | | | | | 45 | | | |
| Lys | Cys | Pro | Phe | Pro | Leu | Ala | Asp | His | Phe | Asn | Ser | Thr | Asn | His | Ala |
| | 50 | | | | | 55 | | | | | 60 | | | | |
| Val | Val | Gln | Thr | Leu | Val | Asn | Asn | Met | Asn | Pro | Gly | Lys | Val | Pro | Lys |
| 65 | | | | | 70 | | | | | 75 | | | | | 80 |
| Ala | Cys | Cys | Val | Pro | Thr | Gln | Leu | Asp | Ser | Val | Ala | Met | Leu | Tyr | Leu |
| | | | | 85 | | | | | 90 | | | | | 95 | |

```
              Asn  Asp  Gln  Ser  Thr  Val  Val  Leu  Lys  Asn  Tyr  Gln  Glu  Met  Thr  Val
                             100                 105                           110

Val  Gly  Cys  Gly  Cys  Arg
                             115
```

( 2 ) INFORMATION FOR SEQ ID NO:16:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: BMP-3

( i x ) FEATURE:
        ( A ) NAME/KEY: Protein
        ( B ) LOCATION: 1..119

( x i ) SEQUENCE DESCRIPTION: SEQ ID NO:16:

```
              Gln  Thr  Leu  Lys  Lys  Ala  Arg  Arg  Lys  Gln  Trp  Ile  Glu  Pro  Arg  Asn
              1                 5                           10                          15

Cys  Ala  Arg  Arg  Tyr  Leu  Lys  Val  Asp  Phe  Ala  Asp  Ile  Gly  Trp  Ser
                             20                 25                           30

Glu  Trp  Ile  Ile  Ser  Pro  Lys  Ser  Phe  Asp  Ala  Tyr  Tyr  Cys  Ser  Gly
                             35                 40                           45

Ala  Cys  Gln  Phe  Pro  Met  Pro  Lys  Ser  Leu  Lys  Pro  Ser  Asn  His  Ala
                             50                 55                           60

Thr  Ile  Gln  Ser  Ile  Val  Arg  Ala  Val  Gly  Val  Val  Pro  Gly  Ile  Pro
              65                                70                          75                     80

Glu  Pro  Cys  Cys  Val  Pro  Glu  Lys  Met  Ser  Ser  Leu  Ser  Ile  Leu  Phe
                                  85                 90                          95

Phe  Asp  Glu  Asn  Lys  Asn  Val  Val  Leu  Lys  Val  Tyr  Pro  Asn  Met  Thr
                             100                 105                         110

Val  Glu  Ser  Cys  Ala  Cys  Arg
                             115
```

( 2 ) INFORMATION FOR SEQ ID NO:17:

( i ) SEQUENCE CHARACTERISTICS:
        ( A ) LENGTH: 115 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: MIS ( i x ) FEATURE:
        ( A ) NAME/KEY: Protein
        ( B ) LOCATION: 1..115

( x i ) SEQUENCE DESCRIPTION: SEQ ID NO:17:

```
              Pro  Gly  Arg  Ala  Gln  Arg  Ser  Ala  Gly  Ala  Thr  Ala  Ala  Asp  Gly  Pro
              1                 5                           10                          15

Cys  Ala  Leu  Arg  Glu  Leu  Ser  Val  Asp  Leu  Arg  Ala  Glu  Arg  Ser  Val
                             20                 25                           30

Leu  Ile  Pro  Glu  Thr  Tyr  Gln  Ala  Asn  Asn  Cys  Gln  Gly  Val  Cys  Gly
                             35                 40                           45

Trp  Pro  Gln  Ser  Asp  Arg  Asn  Pro  Arg  Tyr  Gly  Asn  His  Val  Val  Leu
```

```
                    50                          55                          60
    Leu   Leu   Lys   Met   Gln   Ala   Arg   Gly   Ala   Ala   Leu   Ala   Arg   Pro   Pro   Cys
    65                          70                          75                          80

Cys   Val   Pro   Thr   Ala   Tyr   Ala   Gly   Lys   Leu   Leu   Ile   Ser   Leu   Ser   Glu
                                85                          90                          95

Glu   Arg   Ile   Ser   Ala   His   His   Val   Pro   Asn   Met   Val   Ala   Thr   Glu   Cys
                                100                         105                         110

Gly   Cys   Arg
                            115
```

( 2 ) INFORMATION FOR SEQ ID NO:18:

( i ) SEQUENCE CHARACTERISTICS:
        ( A ) LENGTH: 121 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Inhibin alpha ( i x ) FEATURE:
        ( A ) NAME/KEY: Protein
        ( B ) LOCATION: 1..121

( x i ) SEQUENCE DESCRIPTION: SEQ ID NO:18:

```
    Leu   Arg   Leu   Leu   Gln   Arg   Pro   Pro   Glu   Glu   Pro   Ala   Ala   His   Ala   Asn
    1                           5                           10                          15

Cys   His   Arg   Val   Ala   Leu   Asn   Ile   Ser   Phe   Gln   Glu   Leu   Gly   Trp   Glu
                                20                          25                          30

Arg   Trp   Ile   Val   Tyr   Pro   Pro   Ser   Phe   Ile   Phe   His   Tyr   Cys   His   Gly
                        35                          40                          45

Gly   Cys   Gly   Leu   His   Ile   Pro   Pro   Asn   Leu   Ser   Leu   Pro   Val   Pro   Gly
                50                          55                          60

Ala   Pro   Pro   Thr   Pro   Ala   Gln   Pro   Tyr   Ser   Leu   Leu   Pro   Gly   Ala   Gln
    65                          70                          75                          80

Pro   Cys   Cys   Ala   Ala   Leu   Pro   Gly   Thr   Met   Arg   Pro   Leu   His   Val   Arg
                                85                          90                          95

Thr   Thr   Ser   Asp   Gly   Gly   Tyr   Ser   Phe   Lys   Tyr   Glu   Thr   Val   Pro   Asn
                                100                         105                         110

Leu   Leu   Thr   Gln   His   Cys   Ala   Cys   Ile
                        115                         120
```

( 2 ) INFORMATION FOR SEQ ID NO:19:

( i ) SEQUENCE CHARACTERISTICS:
        ( A ) LENGTH: 121 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Inhibin betaA ( i x ) FEATURE:
        ( A ) NAME/KEY: Protein
        ( B ) LOCATION: 1..121

( x i ) SEQUENCE DESCRIPTION: SEQ ID NO:19:

```
    Arg   Arg   Arg   Arg   Arg   Gly   Leu   Glu   Cys   Asp   Gly   Lys   Val   Asn   Ile   Cys
    1                           5                           10                          15
```

```
         Cys  Lys  Lys  Gln  Phe  Phe  Val  Ser  Phe  Lys  Asp  Ile  Gly  Trp  Asn  Asp
                        20                       25                      30

Trp  Ile  Ile  Ala  Pro  Ser  Gly  Tyr  His  Ala  Asn  Tyr  Cys  Glu  Gly  Glu
                        35                       40                      45

Cys  Pro  Ser  His  Ile  Ala  Gly  Thr  Ser  Gly  Ser  Ser  Leu  Ser  Phe  His
              50                       55                      60

Ser  Thr  Val  Ile  Asn  His  Tyr  Arg  Met  Arg  Gly  His  Ser  Pro  Phe  Ala
         65                       70                      75                           80

Asn  Leu  Lys  Ser  Cys  Cys  Val  Pro  Thr  Lys  Leu  Arg  Pro  Met  Ser  Met
                             85                       90                      95

Leu  Tyr  Tyr  Asp  Asp  Gly  Gln  Asn  Ile  Ile  Lys  Lys  Asp  Ile  Gln  Asn
                        100                      105                     110

Met  Ile  Val  Glu  Glu  Cys  Gly  Cys  Ser
                        115                      120
```

( 2 ) INFORMATION FOR SEQ ID NO:20:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Inhibin betaB ( i x ) FEATURE:
        ( A ) NAME/KEY: Protein
        ( B ) LOCATION: 1..120

( x i ) SEQUENCE DESCRIPTION: SEQ ID NO:20:

```
         Arg  Ile  Arg  Lys  Arg  Gly  Leu  Glu  Cys  Asp  Gly  Arg  Thr  Asn  Leu  Cys
         1                   5                       10                      15

Cys  Arg  Gln  Gln  Phe  Phe  Ile  Asp  Phe  Arg  Leu  Ile  Gly  Trp  Asn  Asp
                        20                       25                      30

Trp  Ile  Ile  Ala  Pro  Thr  Gly  Tyr  Tyr  Gly  Asn  Tyr  Cys  Glu  Gly  Ser
                        35                       40                      45

Cys  Pro  Ala  Tyr  Leu  Ala  Gly  Val  Pro  Gly  Ser  Ala  Ser  Ser  Phe  His
              50                       55                      60

Thr  Ala  Val  Val  Asn  Gln  Tyr  Arg  Met  Arg  Gly  Leu  Asn  Pro  Gly  Thr
         65                       70                      75                           80

Val  Asn  Ser  Cys  Cys  Ile  Pro  Thr  Lys  Leu  Ser  Thr  Met  Ser  Met  Leu
                             85                       90                      95

Tyr  Phe  Asp  Asp  Glu  Tyr  Asn  Ile  Val  Lys  Arg  Asp  Val  Pro  Asn  Met
                        100                      105                     110

Ile  Val  Glu  Glu  Cys  Gly  Cys  Ala
                        115                      120
```

( 2 ) INFORMATION FOR SEQ ID NO:21:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: TGF-beta1

( i x ) FEATURE:
    ( A ) NAME/KEY: Protein
    ( B ) LOCATION: 1..114

( x i ) SEQUENCE DESCRIPTION: SEQ ID NO:21:

```
Arg Arg Ala Leu Asp Thr Asn Tyr Cys Phe Ser Ser Thr Glu Lys Asn
1               5                   10                  15
Cys Cys Val Arg Gln Leu Tyr Ile Asp Phe Arg Lys Asp Leu Gly Trp
            20                  25                  30
Lys Trp Ile His Glu Pro Lys Gly Tyr His Ala Asn Phe Cys Leu Gly
            35                  40                  45
Pro Cys Pro Tyr Ile Trp Ser Leu Asp Thr Gln Tyr Ser Lys Val Leu
    50                  55                  60
Ala Leu Tyr Asn Gln His Asn Pro Gly Ala Ser Ala Ala Pro Cys Cys
65                  70                  75                  80
Val Pro Gln Ala Leu Glu Pro Leu Pro Ile Val Tyr Tyr Val Gly Arg
                85                  90                  95
Lys Pro Lys Val Glu Gln Leu Ser Asn Met Ile Val Arg Ser Cys Lys
                100                 105                 110
Cys Ser
```

( 2 ) INFORMATION FOR SEQ ID NO:22:

( i ) SEQUENCE CHARACTERISTICS:
    ( A ) LENGTH: 114 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( B ) CLONE: TGF-beta2

( i x ) FEATURE:
    ( A ) NAME/KEY: Protein
    ( B ) LOCATION: 1..114

( x i ) SEQUENCE DESCRIPTION: SEQ ID NO:22:

```
Lys Arg Ala Leu Asp Ala Ala Tyr Cys Phe Arg Asn Val Gln Asp Asn
1               5                   10                  15
Cys Cys Leu Arg Pro Leu Tyr Ile Asp Phe Lys Arg Asp Leu Gly Trp
            20                  25                  30
Lys Trp Ile His Glu Pro Lys Gly Tyr Asn Ala Asn Phe Cys Ala Gly
            35                  40                  45
Ala Cys Pro Tyr Leu Trp Ser Ser Asp Thr Gln His Ser Arg Val Leu
    50                  55                  60
Ser Leu Tyr Asn Thr Ile Asn Pro Glu Ala Ser Ala Ser Pro Cys Cys
65                  70                  75                  80
Val Ser Gln Asp Leu Glu Pro Leu Thr Ile Leu Tyr Tyr Ile Gly Lys
                85                  90                  95
Thr Pro Lys Ile Glu Gln Leu Ser Asn Met Ile Val Lys Ser Cys Lys
                100                 105                 110
Cys Ser
```

( 2 ) INFORMATION FOR SEQ ID NO:23:

( i ) SEQUENCE CHARACTERISTICS:
    ( A ) LENGTH: 114 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
   ( B ) CLONE: TGF-beta3

( i x ) FEATURE:
   ( A ) NAME/KEY: Protein
   ( B ) LOCATION: 1..114

( x i ) SEQUENCE DESCRIPTION: SEQ ID NO:23:

| Lys | Arg | Ala | Leu | Asp | Thr | Asn | Tyr | Cys | Phe | Arg | Asn | Leu | Glu | Glu | Asn |
|---|---|---|---|---|---|---|---|---|---|---|---|---|---|---|---|
| 1 | | | | 5 | | | | | 10 | | | | | 15 | |
| Cys | Cys | Val | Arg | Pro | Leu | Tyr | Ile | Asp | Phe | Arg | Gln | Asp | Leu | Gly | Trp |
| | | | 20 | | | | | 25 | | | | | 30 | | |
| Lys | Trp | Val | His | Glu | Pro | Lys | Gly | Tyr | Tyr | Ala | Asn | Phe | Cys | Ser | Gly |
| | | | 35 | | | | | 40 | | | | | 45 | | |
| Pro | Cys | Pro | Tyr | Leu | Arg | Ser | Ala | Asp | Thr | Thr | His | Ser | Thr | Val | Leu |
| | | 50 | | | | | 55 | | | | | 60 | | | |
| Gly | Leu | Tyr | Asn | Thr | Leu | Asn | Pro | Glu | Ala | Ser | Ala | Ser | Pro | Cys | Cys |
| 65 | | | | | 70 | | | | | 75 | | | | | 80 |
| Val | Pro | Gln | Asp | Leu | Glu | Pro | Leu | Thr | Ile | Leu | Tyr | Tyr | Val | Gly | Arg |
| | | | | 85 | | | | | 90 | | | | | 95 | |
| Thr | Pro | Lys | Val | Glu | Gln | Leu | Ser | Asn | Met | Val | Val | Lys | Ser | Cys | Lys |
| | | | 100 | | | | | 105 | | | | | 110 | | |
| Cys | Ser | | | | | | | | | | | | | | |

( 2 ) INFORMATION FOR SEQ ID NO:24:

( i ) SEQUENCE CHARACTERISTICS:
    ( A ) LENGTH: 116 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( B ) CLONE: TGF-beta4

( i x ) FEATURE:
    ( A ) NAME/KEY: Protein
    ( B ) LOCATION: 1..116

( x i ) SEQUENCE DESCRIPTION: SEQ ID NO:24:

| Arg | Arg | Asp | Leu | Asp | Thr | Asp | Tyr | Cys | Phe | Gly | Pro | Gly | Thr | Asp | Glu |
|---|---|---|---|---|---|---|---|---|---|---|---|---|---|---|---|
| 1 | | | | 5 | | | | | 10 | | | | | 15 | |
| Lys | Asn | Cys | Cys | Val | Arg | Pro | Leu | Tyr | Ile | Asp | Phe | Arg | Lys | Asp | Leu |
| | | | 20 | | | | | 25 | | | | | 30 | | |
| Gln | Trp | Lys | Trp | Ile | His | Glu | Pro | Lys | Gly | Tyr | Met | Ala | Asn | Phe | Cys |
| | | 35 | | | | | 40 | | | | | 45 | | | |
| Met | Gly | Pro | Cys | Pro | Tyr | Ile | Trp | Ser | Ala | Asp | Thr | Gln | Tyr | Thr | Lys |
| | | 50 | | | | | 55 | | | | | 60 | | | |
| Val | Leu | Ala | Leu | Tyr | Asn | Gln | His | Asn | Pro | Gly | Ala | Ser | Ala | Ala | Pro |
| 65 | | | | | 70 | | | | | 75 | | | | | 80 |
| Cys | Cys | Val | Pro | Gln | Thr | Leu | Asp | Pro | Leu | Pro | Ile | Ile | Tyr | Tyr | Val |
| | | | | 85 | | | | | 90 | | | | | 95 | |
| Gly | Arg | Asn | Val | Arg | Val | Glu | Gln | Leu | Ser | Asn | Met | Val | Val | Arg | Ala |
| | | | 100 | | | | | 105 | | | | | 110 | | |
| Cys | Lys | Cys | Ser | | | | | | | | | | | | |
| | | 115 | | | | | | | | | | | | | |

( 2 ) INFORMATION FOR SEQ ID NO:25:

( i ) SEQUENCE CHARACTERISTICS:
    ( A ) LENGTH: 114 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( B ) CLONE: TGF-beta5

( i x ) FEATURE:
    ( A ) NAME/KEY: Protein
    ( B ) LOCATION: 1..114

( x i ) SEQUENCE DESCRIPTION: SEQ ID NO:25:

```
Lys Arg Gly Val Gly Gln Glu Tyr Cys Phe Gly Asn Asn Gly Pro Asn
 1               5                  10                 15
Cys Cys Val Lys Pro Leu Tyr Ile Asn Phe Arg Lys Asp Leu Gly Trp
             20                  25                 30
Lys Trp Ile His Glu Pro Lys Gly Tyr Glu Ala Asn Tyr Cys Leu Gly
             35                  40                 45
Asn Cys Pro Tyr Ile Trp Ser Met Asp Thr Gln Tyr Ser Lys Val Leu
     50                  55                  60
Ser Leu Tyr Asn Gln Asn Asn Pro Gly Ala Ser Ile Ser Pro Cys Cys
 65                  70                  75                  80
Val Pro Asp Val Leu Glu Pro Leu Pro Ile Ile Tyr Tyr Val Gly Arg
                 85                  90                  95
Thr Ala Lys Val Glu Gln Leu Ser Asn Met Val Val Arg Ser Cys Asn
                100                 105                 110
Cys Ser
```

( 2 ) INFORMATION FOR SEQ ID NO:26:

( i ) SEQUENCE CHARACTERISTICS:
    ( A ) LENGTH: 454 amino acids
    ( B ) TYPE: amino acid
    ( C ) STRANDEDNESS: single
    ( D ) TOPOLOGY: linear ( i i ) MOLECULE TYPE: protein ( v i i ) IMMEDIATE SOURCE:
    ( B ) CLONE: HUMAN GDF-9

( i x ) FEATURE:
    ( A ) NAME/KEY: Protein
    ( B ) LOCATION: 1..454

( x i ) SEQUENCE DESCRIPTION: SEQ ID NO:26:

```
Met Ala Arg Pro Asn Lys Phe Leu Leu Trp Phe Cys Cys Phe Ala Trp
 1               5                  10                 15
Leu Cys Phe Pro Ile Ser Leu Gly Ser Gln Ala Ser Gly Gly Glu Ala
             20                  25                 30
Gln Ile Ala Ala Ser Ala Glu Leu Glu Ser Gly Ala Met Pro Trp Ser
             35                  40                 45
Leu Leu Gln His Ile Asp Glu Arg Asp Arg Ala Gly Leu Leu Pro Ala
     50                  55                  60
Leu Phe Lys Val Leu Ser Val Gly Arg Gly Gly Ser Pro Arg Leu Gln
 65                  70                  75                  80
Pro Asp Ser Arg Ala Leu His Tyr Met Lys Lys Leu Tyr Lys Thr Tyr
                 85                  90                  95
```

|   |   |   |   |   |   |   |   |   |   |   |   |   |   |   |
|---|---|---|---|---|---|---|---|---|---|---|---|---|---|---|
| Ala | Thr | Lys | Glu<br>100 | Gly | Ile | Pro | Lys | Ser<br>105 | Asn | Arg | Ser | His | Leu<br>110 | Tyr | Asn |
| Thr | Val | Arg<br>115 | Leu | Phe | Thr | Pro | Cys<br>120 | Thr | Arg | His | Lys | Gln<br>125 | Ala | Pro | Gly |
| Asp | Gln<br>130 | Val | Thr | Gly | Ile | Leu<br>135 | Pro | Ser | Val | Glu | Leu<br>140 | Leu | Phe | Asn | Leu |
| Asp<br>145 | Arg | Ile | Thr | Thr | Val<br>150 | Glu | His | Leu | Leu | Lys<br>155 | Ser | Val | Leu | Leu | Tyr<br>160 |
| Asn | Ile | Asn | Asn | Ser<br>165 | Val | Ser | Phe | Ser | Ser<br>170 | Ala | Val | Lys | Cys | Val<br>175 | Cys |
| Asn | Leu | Met | Ile<br>180 | Lys | Glu | Pro | Lys | Ser<br>185 | Ser | Ser | Arg | Thr | Leu<br>190 | Gly | Arg |
| Ala | Pro | Tyr<br>195 | Ser | Phe | Thr | Phe | Asn<br>200 | Ser | Gln | Phe | Glu | Phe<br>205 | Gly | Lys | Lys |
| His | Lys<br>210 | Trp | Ile | Gln | Ile | Asp<br>215 | Val | Thr | Ser | Leu | Leu<br>220 | Gln | Pro | Leu | Val |
| Ala<br>225 | Ser | Asn | Lys | Arg | Ser<br>230 | Ile | His | Met | Ser | Ile<br>235 | Asn | Phe | Thr | Cys | Met<br>240 |
| Lys | Asp | Gln | Leu | Glu<br>245 | His | Pro | Ser | Ala | Gln<br>250 | Asn | Gly | Leu | Phe | Asn<br>255 | Met |
| Thr | Leu | Val | Ser<br>260 | Pro | Ser | Leu | Ile | Leu<br>265 | Tyr | Leu | Asn | Asp | Thr<br>270 | Ser | Ala |
| Gln | Ala | Tyr<br>275 | His | Ser | Trp | Tyr | Ser<br>280 | Leu | His | Tyr | Lys | Arg<br>285 | Arg | Pro | Ser |
| Gln | Gly<br>290 | Pro | Asp | Gln | Glu | Arg<br>295 | Ser | Leu | Ser | Ala | Tyr<br>300 | Pro | Val | Gly | Glu |
| Glu<br>305 | Ala | Ala | Glu | Asp | Gly<br>310 | Arg | Ser | Ser | His | His<br>315 | Arg | His | Arg | Arg | Gly<br>320 |
| Gln | Glu | Thr | Val | Ser<br>325 | Ser | Glu | Leu | Lys | Lys<br>330 | Pro | Leu | Gly | Pro<br>335 | Ala | Ser |
| Phe | Asn | Leu | Ser<br>340 | Glu | Tyr | Phe | Arg | Gln<br>345 | Phe | Leu | Leu | Pro<br>350 | Gln | Asn | Glu |
| Cys | Glu | Leu<br>355 | His | Asp | Phe | Arg | Leu<br>360 | Ser | Phe | Ser | Gln | Leu<br>365 | Lys | Trp | Asp |
| Asn | Trp<br>370 | Ile | Val | Ala | Pro | His<br>375 | Arg | Tyr | Asn | Pro | Arg<br>380 | Tyr | Cys | Lys | Gly |
| Asp<br>385 | Cys | Pro | Arg | Ala | Val<br>390 | Gly | His | Arg | Tyr | Gly<br>395 | Ser | Pro | Val | His | Thr<br>400 |
| Met | Val | Gln | Asn | Ile<br>405 | Ile | Tyr | Glu | Lys | Leu<br>410 | Asp | Ser | Ser | Val<br>415 | Pro | Arg |
| Pro | Ser | Cys | Val<br>420 | Pro | Ala | Lys | Tyr | Ser<br>425 | Pro | Leu | Ser | Val<br>430 | Leu | Thr | Ile |
| Glu | Pro | Asp<br>435 | Gly | Ser | Ile | Ala | Tyr<br>440 | Lys | Glu | Tyr | Glu | Asp<br>445 | Met | Ile | Ala |
| Thr | Lys<br>450 | Cys | Thr | Cys | Arg |   |   |   |   |   |   |   |   |   |   |

I claim:

1. Substantially pure growth differentiation factor-9 (GDF-9) having the amino acid sequence as set forth in SEQ ID NO:4 or SEQ ID NO:26.

2. An isolated polynucleotide encoding GDF-9 polypeptide having an amino acid sequence as set forth in SEQ ID NO:4 or SEQ ID NO:26.

3. The polynucleotide of claim 2, wherein the polynucleotide is isolated from a mammalian cell.

4. The polynucleotide of claim 3, wherein the mammalian cell is selected from the group consisting of mouse, rat, and human cell.

5. An expression vector including the polynucleotide of claim 2.

6. The vector of claim 5, wherein the vector is a plasmid.

7. The vector of claim 5, wherein the vector is a viral vector.

8. A host cell containing the vector of claim 5.

9. The host cell of claim 8, wherein the cell is prokaryotic.

10. The host cell of claim 8, wherein the cell is eukaryotic.

11. An isolated polynucleotide selected from the group consisting of:
   a) SEQ ID NO:3;
   b) SEQ ID NO:3, wherein T can also be U;
   c) nucleic sequences complementary to SEQ ID NO:3; and
   d) fragments of a), b), or c) that are at least 15 bases in length and that will hybridize to DNA which encodes the GDF-9 protein of SEQ ID NO:4 or SEQ ID NO:26.

12. A method for detecting an oocyte in a sample comprising contacting the sample with a nucleic acid probe which is a fragment as defined in part d) of claim 11 or an antibody which binds to a GDF-9 polypeptide as set forth in SEQ ID NO:4 or SEQ ID NO:26, wherein binding is indicative of the presence of an oocyte.

13. The method of claim 12, wherein the contacting is in vitro.

14. The method of claim 12, wherein the contacting is in situ.

* * * * *